US009051275B2

(12) United States Patent
Berenguer Maimó et al.

(10) Patent No.: US 9,051,275 B2
(45) Date of Patent: Jun. 9, 2015

(54) 4-[-2-[[5-METHYL-1-(2-NAPHTALENYL)-1H-PYRAZOL-3-YL]OXY]ETHYL]MORPHOLINE HYDROCHLORIDE POLYMORPHS AND SOLVATES

(75) Inventors: Ramón Berenguer Maimó, Barcelona (ES); Jorge Medrano Rupérez, Barcelona (ES); Jordi Benet Buchholz, Altafulla (ES); Laura Puig Fernandez, Zaragoza (ES); Laia Pellejà Puxeu, Tarragona (ES)

(73) Assignee: Laboratories Del Dr. Esteve, S.A., Barcelona (ES)

( * ) Notice: Subject to any disclaimer, the term of this patent is extended or adjusted under 35 U.S.C. 154(b) by 0 days.

(21) Appl. No.: 13/577,078

(22) PCT Filed: Feb. 4, 2011

(86) PCT No.: PCT/EP2011/051630
§ 371 (c)(1),
(2), (4) Date: Aug. 30, 2012

(87) PCT Pub. No.: WO2011/095579
PCT Pub. Date: Aug. 11, 2011

(65) Prior Publication Data
US 2012/0316336 A1 Dec. 13, 2012

(30) Foreign Application Priority Data

Feb. 4, 2010 (EP) .................................... 10382025
Aug. 9, 2010 (EP) .................................... 10382226

(51) Int. Cl.
| | |
|---|---|
| C07D 413/12 | (2006.01) |
| C07D 231/22 | (2006.01) |
| A61K 31/4152 | (2006.01) |
| A61P 9/00 | (2006.01) |

(52) U.S. Cl.
CPC .......... *C07D 231/22* (2013.01); *A61K 31/4152* (2013.01)

(58) Field of Classification Search
USPC ....................................... 544/111; 514/236.5
See application file for complete search history.

(56) References Cited

U.S. PATENT DOCUMENTS 7,696,199 B2 * 4/2010 Laggner et al. ............ 514/227.8

FOREIGN PATENT DOCUMENTS

| | | | |
|---|---|---|---|
| EP | 2 113 501 A1 | | 11/2009 |
| WO | 2006021462 | * | 8/2004 |
| WO | WO 2006/021462 A1 | | 3/2006 |

OTHER PUBLICATIONS

Diaz, et al., J. Med. Chem., 2012, 55 (19), 8211-8224.*
Berge, S.M. et al., "Pharmaceutical Salts", Journal of Pharmaceutical Sciences, 1977, vol. 66, No. 1, pp. 1-19.
Hanner, M. et al., "Purification, molecular cloning, and expression of the mammalian sigma—binding site", Proceedings of the National Academy of the Sciences, 1996, vol. 93, pp. 8072-8077.
Lang, M. et al., "The Use of Polymer Heteronuclei for Crystalline Polymorph Selection", Journal of the American Chemical Society, 2002, vol. 124, No. 50 pp. 14834-14835, S1-S2.
Lee, S. and Hoff, C., "Large-Scale Aspects of Salt Formation: Processing of Intermediates and Final Products", Handbook of Pharmaceutical Salts: Properties, Selection, and Use, 2002, Chapter 8, pp. 191-192, 211-214, Chapter 12, 265-266, 282-283.
Price, C.P. et al., "Crystalline Polymorph Selection and Discovery with Polymer Heteronuclei", Journal of the American Chemical Society, 2005, vol. 127, No. 15, pp. 5512-5517, S1-S7.
Quirion, R. et al., "A proposal for the classification of sigma binding sites", Trends in Pharmacological Science, 1992, vol. 13, pp. 85-86.
Snyder, S.H. and Largent, B.L., "Receptor Mechanisms in Antipsychotic Drug Action: Focus on Sigma Receptors", Journal of Neuropsychiatry, 1989, vol. 1, No. 1, pp. 7-15.
Walker, J.M. et al., "Sigma Receptors: Biology and Function", Pharmacological Reviews, 1990, vol. 42, No. 4, pp. 355-402.
International Search Report issued by the International Searching Authority (ISA/O.E.P.M.) on May 4, 2011 in connection with International Application No. PCT/EP2011/051630.
Rodríguez-Spong, B. et al., "General principles of pharmaceutical solid polymorphism: a supramolecular perspective", Advanced Drug Delivery Reviews, vol. 56 (2004) pp. 241-274.
Vippagunta, S. R. et al., "Crystalline solids", Advanced Drug Delivery Reviews, vol. 48 (2001) pp. 3-26.
Anderson B. D. and Flora K. P., "Preparation of Water-Soluble Compounds Through Salt Formation" The Practice of Medicinal Chemistry, Chapter 34, pp. 739-754 (1996).
Ming L.C., "Screening Polymorphic Forms of Drug Substances by Using Generalized Crystallization Techniques", May 2007 (English language Translation of Abstract).

* cited by examiner

*Primary Examiner* — James O Wilson
*Assistant Examiner* — Cecilia M Jaisle
(74) *Attorney, Agent, or Firm* — Gary J. Gershik; Cooper & Dunham LLP

(57) ABSTRACT

The present invention relates to polymorphs and solvates of the hydrochloride salt of 4-[2-[[5-methyl-1-(2-naphthalenyl)-1H-pyrazol-3-yl]oxy]ethyl]morpholine (P027), processes for their preparation, and to pharmaceutical compositions comprising them.

29 Claims, 41 Drawing Sheets

4-[-2-[[5-METHYL-1-(2-NAPHTALENYL)-1H-PYRAZOL-3-YL]OXY]ETHYL]MORPHOLINE HYDROCHLORIDE POLYMORPHS AND SOLVATES

RELATED APPLICATIONS

This application is a §371 national stage of PCT International Application No. PCT/EP2011/051630, filed Feb. 4, 2011, claiming priority of European Patent Application Nos. EP 10 382 226.8, filed Aug. 9, 2010 and EP 10 382 025.4, filed Feb. 4, 2010, the contents of each of which are hereby incorporated by reference into this application.

FIELD OF THE INVENTION

The present invention relates to polymorphs and solvates of the hydrochloride salt of 4-[2-[[5-methyl-1-(2-naphthalenyl)-1H-pyrazol-3-yl]oxy]ethyl]morpholine (P027), processes for their preparation, and to pharmaceutical compositions comprising them.

BACKGROUND

The search for new therapeutic agents has been greatly aided in recent years by better understanding of the structure of proteins and other biomolecules associated with target diseases. One important class of these proteins is the sigma (σ) receptor, a cell surface receptor of the central nervous system (CNS) which may be related to the dysphoric, hallucinogenic and cardiac stimulant effects of opioids. From studies of the biology and function of sigma receptors, evidence has been presented that sigma receptor ligands may be useful in the treatment of psychosis and movement disorders such as dystonia and tardive dyskinesia, and motor disturbances associated with Huntington's chorea or Tourette's syndrome and in Parkinson's disease (Walker, J. M. et al, Pharmacological Reviews, 1990, 42, 355). It has been reported that the known sigma receptor ligand rimazole clinically shows effects in the treatment of psychosis (Snyder, S. H., Largent, B. L. J. Neuropsychiatry 1989, 1, 7). The sigma binding sites have preferential affinity for the dextrorotatory isomers of certain opiate benzomorphans, such as (+)SKF 10047, (+)cyclazocine, and (+)pentazocine and also for some narcoleptics such as haloperidol.

The sigma receptor has at least two subtypes, which may be discriminated by stereoselective isomers of these pharmacoactive drugs. SKF 10047 has nanomolar affinity for the sigma 1 (σ-1) site, and has micromolar affinity for the sigma 2 (σ-2) site. Haloperidol has similar affinities for both subtypes. Endogenous sigma ligands are not known, although progesterone has been suggested to be one of them. Possible sigma-site-mediated drug effects include modulation of glutamate receptor function, neurotransmitter response, neuroprotection, behavior, and cognition (Quirion, R. et al. Trends Pharmacol. Sci., 1992, 13:85-86). Most studies have implied that sigma binding sites (receptors) are plasmalemmal elements of the signal transduction cascade. Drugs reported to be selective sigma ligands have been evaluated as antipsychotics (Hanner, M. et al. Proc. Natl. Acad. Sci., 1996, 93:8072-8077). The existence of sigma receptors in the CNS, immune and endocrine systems have suggested a likelihood that it may serve as link between the three systems.

In view of the potential therapeutic applications of agonists or antagonists of the sigma receptor, a great effort has been directed to find selective ligands. Thus, the prior art discloses different sigma receptor ligands. 4-[2-[[5-methyl-1-(2-naphthalenyl)-1H-pyrazol-3-yl]oxy]ethyl]morpholine is one of such promising sigma receptor ligands. The compound and its synthesis are disclosed and claimed in WO2006/021462.

4-[2-[([5-methyl-1-(2-naphthalenyl)-1H-pyrazol-3-yl]oxy]ethyl]morpholine is a highly selective sigma-1 (σ-1) receptor antagonist. It has displayed strong analgesic activity in the treatment and prevention of chronic and acute pain, and particularly, neuropathic pain. The compound has a molecular weight 337.42 uma. The structural formula of the compound is:

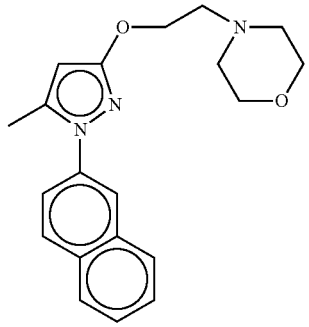

The solid state physical properties of a pharmaceutical compound can be influenced by the conditions under which the compound is obtained in solid form. Solid state physical properties include, for example, the flowability of the milled solid which affects the ease with which the compound is handled during processing into a pharmaceutical product. Another important solid state property of a pharmaceutical compound is its rate of dissolution in aqueous fluid. The rate of dissolution of an active ingredient in a patient's stomach fluid can have therapeutic consequences because it imposes an upper limit on the rate at which an orally administered active ingredient can reach the blood. The solid-state form of a compound may also affect its solubility, bioavailability, behavior on compaction, stability, or its electrostatic nature.

Polymorphism is the property of some molecules and molecular complexes to assume more than one crystalline or amorphous form in the solid state. In general, polymorphism is caused by the ability of the molecule of a substance to change its conformation or to form different inter molecular and intramolecular interactions, particularly hydrogen bonds, which is reflected in different atom arrangements in the crystal lattices of different polymorphs. Accordingly, polymorphs are distinct solids sharing the same molecular Formula, having distinct advantageous and/or disadvantageous physical properties compared to other forms in the polymorph family.

The term "solvate" refers to any solid form of a given compound in which said compound is bonded by a non-covalent bond to molecule(s) of solvent (normally a polar solvent).

The discovery of new crystalline polymorphic or amorphous forms of a pharmaceutical compound provides an opportunity to improve the physical or performance characteristics of a pharmaceutical product in that it enlarges the repertoire of materials that a formulation scientist has available for designing, for example, a pharmaceutical dosage form of a drug with a targeted release profile or other desired characteristics.

Therefore, there is still a need in the art for additional forms of 4-[2-[[5-methyl-1-(2-naphthalenyl)-1H-pyrazol-3-yl] oxy]ethyl]morpholine to carry out its pharmaceutical development and release its potential, and facilitate the preparation of better formulations of this active pharmaceutical ingredient. In this regard, different morphological forms of the compound may have widely different properties such as, for example, enhanced thermodynamic stability, higher purity or improved bioavailability (e.g. better absorption, dissolution patterns) and could either become intermediates for other forms or provide in themselves a still better formulation of this active pharmaceutical ingredient. Specific compound forms could also facilitate the manufacturing (e.g. enhanced flowability), handling and storage (e.g. non-hygroscopic, long shelf life) of the compound formulations or allow the use of a lower dose of the therapeutic agent, thus decreasing its potential side effects. Thus it is important to find such forms, having desirable properties for pharmaceutical use.

BRIEF DESCRIPTION OF THE INVENTION

The inventors of the present invention have surprisingly found and demonstrated that new solid forms of the hydrochloride salt of 4-[2-[[5-methyl-1-(2-naphthalenyl)-1H-pyrazol-3-yl]oxy]ethyl]morpholine (P027) may achieve one or more of the above mentioned objectives. The novel polymorphic and solvated forms of P027 herein disclosed are fairly stable over the time and have good flow and dissolution characteristics. Particularly, a novel and highly stable crystalline form of the P027 compound (phase I form) provides advantageous production, handling, storage and therapeutic properties. Further, some of the new solid forms of P027 may be useful as intermediates for other useful forms such as the crystalline phase I form of P027.

Thus, the present invention relates to polymorphic forms and solvates of P027, to their use and to several processes for their preparation.

The hydrochloride salt of 4-[2-[[5-methyl-1-(2-naphthalenyl)-1H-pyrazol-3-yl]oxy]ethyl]morpholine (P027) can be prepared by contacting a solution of the base with hydrochloric acid. The P027 compound has a molecular weight 373.88 uma, a pKa of 6.73 and a melting point of 194.2° C. The compound is very soluble in water and freely soluble in methanol, 1N hydrochloric acid and dimethyl sulphoxide. It is sparingly soluble in ethanol, slightly soluble in acetone and practically insoluble in ethyl acetate and in 1N sodium hydroxide. The product exhibits a better dissolution and absorption profile in vivo than its related base.

In one embodiment, the present invention is directed to a solid polymorphic or solvated form of the hydrochloride salt of 4-[2-[[5-methyl-1-(2-naphthalenyl)-1H-pyrazol-3-yl]oxy]ethyl]morpholine.

Preferably, said solid form is selected from the group consisting of:

P027 phase I form, which can be characterized because it has a X-ray powder diffraction pattern showing characteristic peaks at a reflection angle [2θ] of about 5.9, 8.1, 11.3, 11.7, 14.2, 15.1, 15.8, 16.3, 16.8, 17.8, 18.1, 18.6, 19.8, 20.9, 21.9, 22.8, 23.0, 23.2, 23.6, 23.9, 24.3, 25.0, 25.1, 28.0, 28.3, 28.6, 29.0, 29.2, 30.7, and 30.9, with the 2θ values being obtained using copper radiation ($Cu_{K\alpha 1}$ 1.54060 Å).

P027 phase II form, which can be characterized because it has a X-ray powder diffraction pattern showing characteristic peaks at a reflection angle [2θ] of about the values indicated below in table 1:

TABLE 1

List of selected peaks obtained by powder X-Ray diffraction of phase II

| Angle (2θ) | d value (Å) | Intensity (%) |
|---|---|---|
| 5.776 | 15.28888 | 30.2 |
| 11.629 | 7.60368 | 8.3 |
| 14.558 | 6.07960 | 4.4 |
| 15.737 | 5.62658 | 73.1 |
| 15.891 | 5.57256 | 37.3 |
| 16.420 | 5.39408 | 14.1 |
| 16.740 | 5.29166 | 12.7 |
| 17.441 | 5.08075 | 23.7 |
| 17.635 | 5.02527 | 100.0 |
| 18.056 | 4.90895 | 44.8 |
| 18.219 | 4.86548 | 23.3 |
| 19.232 | 4.61143 | 22.9 |
| 19.712 | 4.50004 | 4.4 |
| 20.140 | 4.40556 | 2.8 |
| 20.685 | 4.29064 | 4.3 |
| 21.135 | 4.20016 | 7.6 |
| 21.889 | 4.05717 | 33.0 |
| 22.108 | 4.01757 | 46.8 |
| 22.478 | 3.95233 | 8.8 |
| 22.763 | 3.90336 | 14.1 |
| 23.219 | 3.82779 | 13.5 |
| 23.454 | 3.78998 | 21.3 |
| 23.782 | 3.73840 | 12.6 |
| 24.689 | 3.60310 | 15.6 |
| 25.065 | 3.54983 | 10.6 |
| 25.671 | 3.46750 | 13.7 |

P027 phase III form, which can be characterized because it has a X-ray powder diffraction pattern showing characteristic peaks at a reflection angle [2θ] of about the values indicated below in table 2:

TABLE 2

List of selected peaks obtained by powder X-Ray diffraction of phase III

| Angle (2θ) | d value (Å) | Intensity (%) |
|---|---|---|
| 5.437 | 16.24165 | 14.9 |
| 5.714 | 15.45508 | 31.2 |
| 10.918 | 8.09724 | 1.9 |
| 11.546 | 7.65777 | 3.4 |
| 12.704 | 6.96243 | 2.3 |
| 13.344 | 6.63006 | 7.3 |
| 13.984 | 6.32777 | 6.0 |
| 14.505 | 6.10193 | 3.7 |
| 15.606 | 5.67363 | 24.1 |
| 15.824 | 5.59613 | 61.7 |
| 16.164 | 5.47909 | 40.3 |
| 16.646 | 5.32137 | 5.1 |
| 17.333 | 5.11195 | 8.3 |
| 17.837 | 4.96880 | 80.1 |
| 18.719 | 4.73663 | 62.4 |
| 18.878 | 4.69703 | 38.3 |
| 19.236 | 4.61037 | 10.2 |
| 19.533 | 4.54088 | 25.1 |
| 20.142 | 4.40496 | 20.3 |
| 20.689 | 4.28973 | 15.8 |
| 21.337 | 4.16103 | 4.2 |
| 22.008 | 4.03562 | 13.9 |
| 22.929 | 3.87545 | 19.6 |
| 23.596 | 3.76747 | 100.0 |
| 24.748 | 3.59457 | 10.1 |
| 25.064 | 3.55008 | 35.7 |
| 25.207 | 3.53024 | 47.7 |
| 25.737 | 3.45874 | 25.5 |
| 26.148 | 3.40521 | 66.9 |

P027 phase IV form, which can be characterized because it has a X-ray powder diffraction pattern showing characteristic peaks at a reflection angle [2θ] of about the values indicated below in table 3:

TABLE 3

List of selected peaks obtained by powder X-Ray diffraction of phase IV

| Angle (2θ) | d value (Å) | Intensity (%) |
|---|---|---|
| 5.805 | 15.21150 | 51.5 |
| 11.685 | 7.56709 | 30.4 |
| 15.559 | 5.69074 | 84.9 |
| 15.804 | 5.60321 | 7.1 |
| 16.397 | 5.40173 | 49.5 |
| 16.879 | 5.24838 | 47.7 |
| 17.357 | 5.10514 | 39.2 |
| 17.465 | 5.07372 | 42.4 |
| 17.621 | 5.02921 | 66.8 |
| 19.112 | 4.64012 | 100.0 |
| 19.435 | 4.56373 | 3.8 |
| 19.923 | 4.45292 | 16.1 |
| 21.224 | 4.18278 | 10.9 |
| 21.987 | 4.03934 | 83.5 |
| 22.167 | 4.00707 | 45.4 |
| 22.412 | 3.96379 | 33.8 |
| 22.852 | 3.88840 | 18.0 |
| 23.059 | 3.85401 | 14.4 |
| 23.359 | 3.80517 | 61.8 |
| 23.855 | 3.72720 | 13.6 |
| 24.092 | 3.69105 | 29.7 |
| 25.722 | 3.46066 | 16.4 |
| 26.054 | 3.41730 | 10.8 |
| 26.649 | 3.34237 | 16.3 |
| 27.780 | 3.20885 | 4.2 |

P027 dioxane solvate, which can be characterized because it has a X-ray powder diffraction pattern showing characteristic peaks at a reflection angle [2θ] of about the values indicated below in table 4:

TABLE 4

List of selected peaks obtained by powder X-Ray diffraction of the dioxane solvate

| Angle (2θ) | d value (Å) | Intensity (%) |
|---|---|---|
| 4.734 | 18.65133 | 12.1 |
| 9.317 | 9.48417 | 17.2 |
| 11.390 | 7.76280 | 14.5 |
| 13.614 | 6.49913 | 6.8 |
| 14.290 | 6.19322 | 6.6 |
| 14.815 | 5.97468 | 47.7 |
| 16.211 | 5.46334 | 17.2 |
| 16.432 | 5.39027 | 15.0 |
| 16.782 | 5.27852 | 5.4 |
| 17.741 | 4.99534 | 4.4 |
| 18.056 | 4.90904 | 9.2 |
| 18.329 | 4.83643 | 9.2 |
| 18.724 | 4.73540 | 82.7 |
| 19.070 | 4.65016 | 44.1 |
| 19.494 | 4.55001 | 4.5 |
| 20.436 | 4.34235 | 21.4 |
| 20.762 | 4.27483 | 18.4 |
| 21.587 | 4.11339 | 26.7 |
| 22.000 | 4.03705 | 100.0 |
| 22.935 | 3.87457 | 24.2 |
| 23.084 | 3.84979 | 22.3 |
| 23.551 | 3.77450 | 14.0 |
| 23.891 | 3.72152 | 5.6 |
| 24.721 | 3.59850 | 3.6 |
| 25.078 | 3.54803 | 13.2 |

P027 chloroform solvate, which can be characterized because it has a X-ray powder diffraction pattern showing characteristic peaks at a reflection angle [2θ] of about the values indicated below in table 5:

TABLE 5

List of selected peaks obtained by powder X-Ray diffraction of the chloroform solvate

| Angle (2θ) | d value (Å) | Intensity (%) |
|---|---|---|
| 11.370 | 7.77642 | 10.0 |
| 13.396 | 6.60439 | 0.9 |
| 14.048 | 6.29920 | 1.1 |
| 15.010 | 5.89751 | 33.5 |
| 15.303 | 5.78539 | 4.0 |
| 16.117 | 5.49492 | 4.2 |
| 16.804 | 5.27165 | 1.5 |
| 17.040 | 5.19923 | 6.6 |
| 17.830 | 4.97065 | 2.1 |
| 18.029 | 4.91633 | 8.4 |
| 18.661 | 4.75106 | 11.3 |
| 18.859 | 4.70167 | 7.1 |
| 19.190 | 4.62136 | 2.9 |
| 20.150 | 4.40334 | 3.1 |
| 20.434 | 4.34278 | 1.1 |
| 21.424 | 4.14416 | 2.5 |
| 22.279 | 3.98707 | 100.0 |
| 22.871 | 3.88527 | 16.8 |
| 23.449 | 3.79074 | 9.1 |
| 23.918 | 3.71738 | 0.9 |
| 24.343 | 3.65347 | 3.1 |
| 24.709 | 3.60019 | 4.6 |
| 24.820 | 3.58439 | 1.8 |
| 25.459 | 3.49576 | 16.4 |
| 26.199 | 3.39873 | 7.6 |

According to another embodiment, the crystalline P027 phase I form of 4-[2-[[5-methyl-1-(2-naphthalenyl)-1H-pyrazol-3-yl]oxy]ethyl]morpholine hydrochloride according to the present invention has a monoclinic unit cell with the following approximate dimensions:

a=29.4(3)Å
b=11.7(11)Å
c=11.0(10)Å
α=90°
β=91.3 (2)
γ=90°

The preparation of the above polymorphic and solvated forms represents additional embodiments of the present invention.

The P027 phase I form can be prepared by crystallizing the P027 compound in various solvents by means of various techniques such as: solvent evaporation at varying temperatures, crystallization from hot saturated solutions, crystallization by antisolvent addition, crystallization by antisolvent diffusion, crystallization from water and solvents mixtures and the preparation of suspensions.

P027 phase II form may be obtained in polymer induced crystallizations by solvent evaporation.

P027 phase III form may be obtained in polymer induced crystallizations either by solvent evaporation or by crystallization by antisolvent addition.

P027 phase IV form may be obtained in polymer induced crystallizations by crystallization by antisolvent addition.

P027 dioxane solvate may be obtained by solvent drop grinding in dioxane or by crystallization from a hot saturated solution of dioxane.

P027 chloroform solvate may be obtained in polymer induced crystallizations either by solvent (chloroform) evaporation or by crystallization from hot saturated solutions of chloroform.

Another embodiment of the present invention includes the transformation of crystalline forms phase II, phase III and phase IV above into a more stable polymorphic form such as P027 phase I form.

Another embodiment of the present invention includes the transformation of a solvate of P027, preferably chloroform solvate, into a more stable polymorphic form such as phase I form.

A further embodiment of the present invention includes pharmaceutical compositions comprising at least one of the forms of the hydrochloride salt of 4-[2-[[5-methyl-1-(2-naphthalenyl)-1H-pyrazol-3-yl]oxy]ethyl]morpholine abovementioned, particularly P027 phase I, P027 phase II. P027 phase III. P027 phase IV. P027 chloroform solvate and P027 dioxane solvate.

These aspects and preferred embodiments thereof are additionally also defined in the claims.

DETAILED DESCRIPTION OF THE INVENTION

Figure 1:
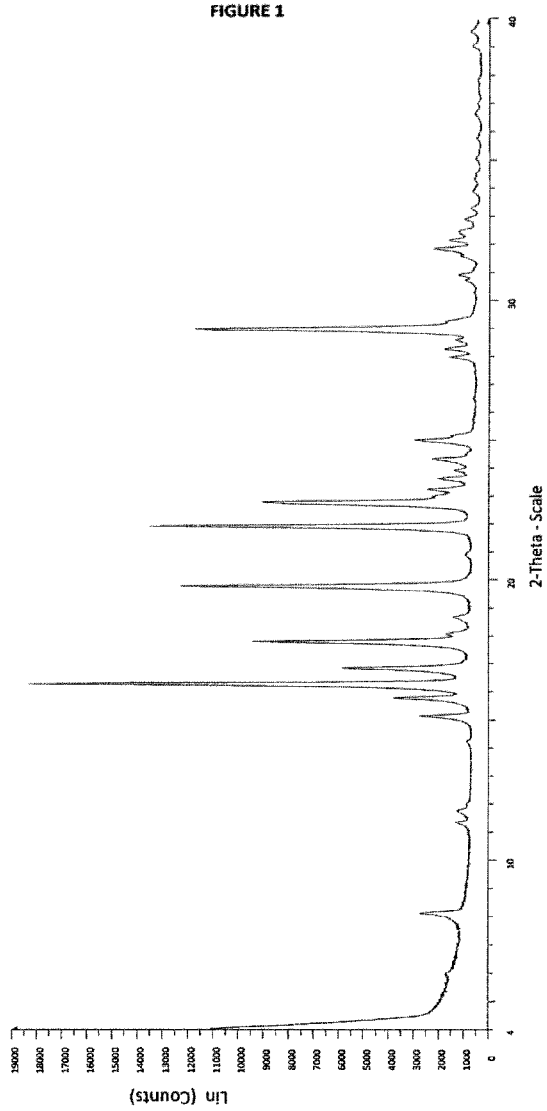
FIG. 1: Standard PXRD pattern of phase I.
Figure 2:
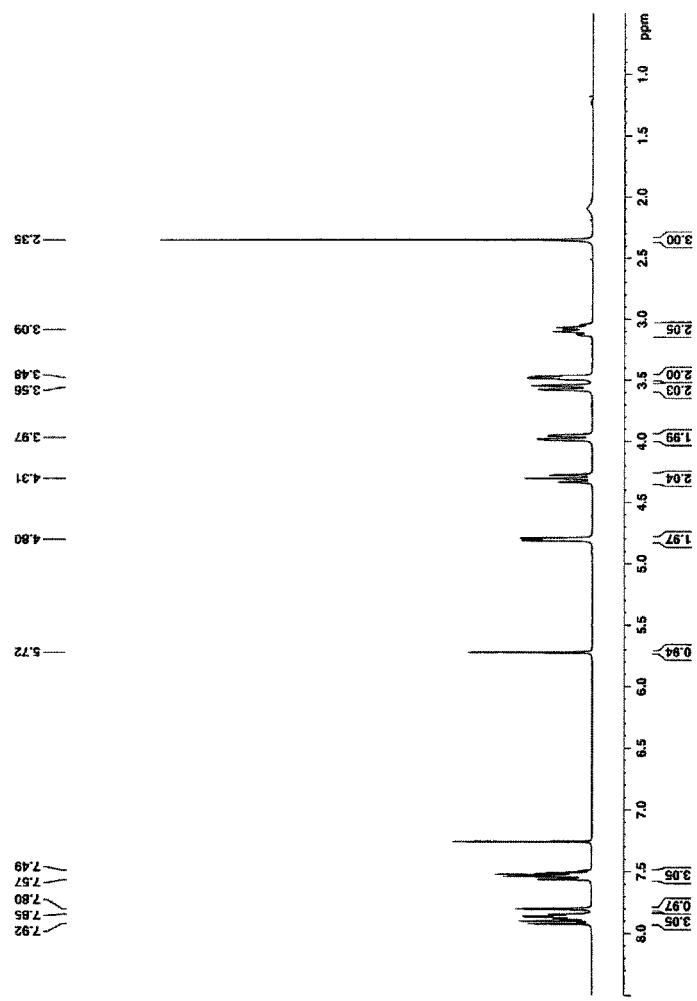
FIG. 2: $^1$H NMR spectrum of a P027 compound solution.

The inventors of the present invention have found novel solid forms of the hydrochloride salt of 4-[2-[[5-methyl-1-(2-naphthalenyl)-1H-pyrazol-3-yl]oxy]ethyl]morpholine (P027) which provide advantageous production, handling, storage and therapeutic properties. These compounds have advantages due to the fact that they are solids, what simplifies isolation, purification and handling. In addition, the phase I form of this compound is highly stable and can be formulated and administered providing stable compositions and good pharmacological properties. Additionally, the new forms of P027 may be used for obtaining other forms, such as crystalline phase I form of P027.

As used herein, the term "about" means a slight variation of the value specified, preferably within 10 percent of the value specified. Nevertheless, the term "about" can mean a higher tolerance of variation depending on for instance the experimental technique used. Said variations of a specified value are understood by the skilled person and are within the context of the present invention. Further, to provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

As used herein, "room temperature" or its abbreviation "rt" is taken to mean 20 to 25° C.

The new forms of P027 herein disclosed were characterized by powder X-ray diffraction (PXRD), proton nuclear magnetic resonance ($^1$H-NMR), differential scanning calorimetry (DSC), thermogravimetric analysis (TGA) and Fourier-transformed infrared spectroscopy. The present invention is directed in one aspect to the new solid forms of P027 in themselves, regardless of the technique used for their characterization. Therefore, the techniques and results provided herein are not intended to limit the present invention, but to serve as characterization of the same. The skilled person will be able, given the guidance and results described herein, to compare and characterize using the available techniques the different polymorphs and solvates of the compound 4-[2-[[5-methyl-1-(2-naphthalenyl)-1H-pyrazol-3-yl]oxy]ethyl]morpholine hydrochloride (P027).

The preparation of solid samples of compound P027 was performed in a set of 40 solvents (table 6). Solvents were selected according to previous experience with the aim to cover a broad range of properties.

TABLE 6

Solvents used in the crystallization screening with the corresponding codes

| Name | Code |
|---|---|
| Dimethylsulfoxide | DMS |
| N,N-Dimethylacetamide | DMA |
| N,N-Dimethylformamide | DMF |
| Xylene | XIL |
| Chlorobenzene | CLB |
| n-Butanol | NBL |
| Methyl isobutyl ketone | MIC |
| Isobutyl acetate | AIB |
| Pyridine | PYR |
| Toluene | TOL |
| 3-Pentanone | POA |
| Propyl acetate | APR |
| Nitromethane | NIM |
| Dioxane | DIX |
| Water | $H_2O$ |
| 2-Butanol | BUL |
| n-Heptane | HEP |
| Dimethylcarbonate | CDM |
| Triethylamine | TEA |
| Isopropyl acetate | AIP |
| Diethoxymethane | DEM |
| 1,2-Dichloroethane | DCE |
| Isopropanol | IPH |
| Acetonitrile | ACN |
| Cyclohexane | CHE |
| Methyl ethyl ketone | MEC |
| Butyl amine | BUA |
| Ethanol | EOH |
| Ethyl acetate | AET |
| 1,1,1-Trichloroethane | TCE |
| n-Hexane | HEX |
| Diisopropyl ether | DIE |
| Tetrahydrofuran | THF |
| Methanol | MOH |
| Chloroform | CLF |
| Methyl acetate | MAC |
| Acetone | ACE |
| Methyl tert-butyl ether | MTE |
| Dimethoxymethane | DMM |
| Dichloromethane | DCM |

In order to plan the crystallization screening, the solubility of P027 was determined at room temperature in the set of solvents of table 6 using the following methodology (table 7): 10 mg of the delivered sample were suspended at room temperature in 0.2 mL of the corresponding solvent and successive additions (initially 0.2 mL and finally 0.5 mL) of solvent until the solid was completely dissolved or up to a maximum of 8 mL were performed. After each solvent addition the suspension was vigorously stirred for 10-15 minutes and visually inspected to determine if the solid was completely dissolved. Solubility ranges are listed in table 7.

TABLE 7

Solubility of P027 in different solvents at room temperature

| Solvent | mg/mL |
|---|---|
| Chloroform | >50 |
| Dimethylsulfoxide | >50 |
| Dimethylformamide | >50 |
| Dichloromethane | >50 |
| Methanol | >50 |
| Butyl amine | >50 |
| Water | >50 |
| N,N-Dimethylacetamide | 25-50 |
| Nitromethane | 25-50 |
| Pyridine | 25-50 |
| Ethanol | 15-25 |
| 1,2-Dichloroethane | 15-25 |
| Acetonitrile[1] | 10-20 |
| n-Butanol[1] | 5-10 |
| Acetone | 4.0-5.0 |
| Isopropanol[1] | 4.0-5.0 |
| 2-Butanol[1] | 3-4 |
| Methyl ethyl ketone[1] | 2-4 |
| 3-Pentanone[2] | 1-2 |
| Dioxane[2] | 1-2 |
| Dimethylcarbonate[2] | 1-2 |
| Tetrahydrofuran | <1.2 |
| Methyl acetate | <1.2 |
| Isobutyl acetate | <1.2 |
| Propyl acetate | <1.2 |
| Xylene | <1.2 |
| Isopropyl acetate | <1.2 |
| Toluene | <1.2 |
| Ethyl acetate | <1.2 |
| 1,1,1-Trichloroethane | <1.2 |
| Methyl isobutyl ketone | <1.2 |
| Methyl tert-butyl ether | <1.2 |
| Dimethoxymethane | <1.2 |
| Cyclohexane | <1.2 |
| Chlorobenzene | <1.2 |
| n-Heptane | <1.2 |
| n-Hexane | <1.2 |
| Diisopropyl ether | <1.2 |
| Triethylamine | <1.2 |
| Diethoxymethane | <1.2 |

[1] The solid was dissolved at 60° C. The solution was left at room temperature and no solid was observed.
[2] The solid was dissolved at 80° C. The solution was left at room temperature and no solid was observed.

The solvents in which P027 was insoluble were used as antisolvents (e.g. those solvents providing a solubility <1.2 mg/mL). For example, n-Heptane (HEP), Methyl tert-butyl ether (MTE) and diisopropyl ether (DIE) were used as antisolvents. The other solvents were used as dissolving solvents in the different crystallization strategies assayed.

In order to cover the broadest crystallization range possible, several crystallization methodologies were employed using the solvents described in table 6. Procedures oriented to obtain the thermodynamically stable phase as well as procedures directed to obtain kinetically favoured phases were used. Moreover, solvent mediated as well as solvent free crystallization procedures were assayed. A list of the crystallization procedures used in this invention is following:
  Solvent evaporation at two rates at room temperature
  Solvent evaporation at different temperatures: −21, 4 and 60° C.
  Crystallization from hot saturated solutions at two cooling rates
  Crystallization aimed to the preparation of hydrates
  Crystallization by addition of an antisolvent
  Crystallization by diffusion of an antisolvent
  Grinding experiments
  Pressure experiments
  Slurry experiments (suspensions)

Additionally to the standard crystallization procedures, a new methodology was used applying polymers to induce the crystallization of new solids. As described in the literature, the use of polymers could favour the formation of new crystalline phases (M. Lang et al. J. Am. Chem. Soc., 2002, 124, 14834; C. Price et al. J. Am. Chem. Soc., 2005, 127, 5512.). Moreover the presence of polymers could support the formation of larger single crystals and stabilize the formation of solvates. A series of polymers (see table 8) were added in catalytic amounts to a solution of P027 and crystallized using the following methodologies:

Solvent evaporation at room temperature

Crystallization from hot saturated solutions

Crystallization by antisolvent addition

Grinding experiments

TABLE 8

Polymers used in this invention

| Name | Code |
|---|---|
| Hydroxipropyl methyl cellulose | HPC |
| Poly(ethylene glycol) | PGY |
| Polyvinyl pyrrolidone | PVP |
| Poly(acrylic acid) | PAA |
| Nylon 6/6 | NYL |
| Polypropylene | PPL |
| Poly(styrene-co-divinylbenzene) | PSV |
| Polyvinylchloride | PVC |
| Poly(tetrafluoroethylene) | PTF |
| Poly(vinyl acetate) | PVA |
| Poly(vinyl alcohol) | PVH |
| Polyacrylamide | PAD |
| Polysulfone | PLS |
| Poly(methyl methacrilate) | PMM |

As used herein referring to polymers, "catalytic amounts" represent a substoichiometric amount of polymer with respect to the compound P027; preferably below a 25% wt of the amount (wt) of compound P027: In a particular embodiment, "catalytic amounts" represent below a 20% wt of the compound P027. In a more particular embodiment, "catalytic amounts" represent below a 10% wt of the compound P027.

All solids obtained using the different crystallization methodologies were characterized by PXRD and classified according to the different PXRD patterns obtained. Further analyses performed were also taken into account for the classification of the solids (see experimental section).

The following forms of P027 were identified and characterized among the solids obtained: P027 phase I form, P027 phase II form, P027 phase III form, P027 phase IV form, P027 dioxane solvate and P027 chloroform solvate.

In one embodiment of the present invention, the P027 phase I form is obtained by dissolving the P027 compound in a suitable solvent and then evaporating the solvent to obtain the phase I crystalline form. According to one variant of this process, the P027 compound is dissolved at a temperature ranging from about room temperature to about 120° C. In another variant to this process, the solvent is evaporated at a temperature ranging from about −21° C. to about 60° C. In a further variant of this process, the P027 solution is allowed to cool down slowly. In yet another variant of this process, the P027 solution is cooled down rapidly.

In another embodiment of the present invention, the P027 phase I form is obtained by mixing a P027 solution and an antisolvent. In a variant of this process, the P027 solution is added to the antisolvent. In another variant of this process, the antisolvent is added to the P027 solution. In an additional variant of this process the P027 solution and the antisolvent are mixed at a temperature ranging from about room temperature to about 90° C.

In an additional embodiment of the present invention, the P027 phase I form is obtained by combining a P027 solution and an antisolvent through diffusion. In a variant of this process, the diffusion is a liquid-liquid diffusion. In another variant of this process, the diffusion is a gas-liquid diffusion.

In another embodiment of the present invention, the P027 phase I form is collected from mixtures of P027, water and solvents.

In yet an additional embodiment of the present invention, the P027 phase I form is obtained from suspensions containing the P027 compound. In variant of this process, the suspension is maintained at a temperature ranging from about room temperature to about 80° C.

In an additional embodiment of the present invention, an hydrochloric acid solution and 4-[2-[[5-methyl-1-(2-naphthalenyl)-1H-pyrazol-3-yl]oxy]ethyl]morpholine are mixed to obtain the P027 compound. Preferably, an antisolvent is added to the mixture to induce the crystallization of the P027 compound.

Various of the embodiments above may require additional steps, such as centrifugation, to further isolate the P027 phase I form.

P027 phase II form, phase III form and phase IV form may be obtained in polymer induced crystallizations either by solvent evaporation or by crystallization by antisolvent addition. Thus, another embodiment of the present invention refers to a process for the preparation of polymorphic forms of the hydrochloride salt of 4-[2-[[5-methyl-1-(2-naphthalenyl)-1H-pyrazol-3-yl]oxy]ethyl]morpholine, comprising:

a) dissolving the hydrochloride salt of 4-[2-[[5-methyl-1-(2-naphthalenyl)-1H-pyrazol-3-yl]oxy]ethyl]morpholine in a suitable solvent or mixture of solvents in the presence of catalytic amounts of a polymer, and b) either evaporating the solvent or solvents or adding an antisolvent.

In a preferred embodiment, P027 phase II form is prepared by evaporation of a solution of P027 in water with the presence of catalytic amounts of poly(vinyl alcohol).

In another preferred embodiment, P027 phase III form is prepared by evaporation of a solution of P027 in water or acetone with the presence of catalytic amounts of poly(ethylene glycol). P027 phase III form may also be conveniently prepared by addition of diisopropyl ether as antisolvent to a solution of P027 in water with the presence of catalytic amounts of poly(ethylene glycol).

In another preferred embodiment, P027 phase IV form is prepared by using chloroform as solvent, diisopropyl ether as antisolvent and the following polymers: polyvinyl pyrrolidone (PVP), poly(acrylic acid) (PAA), polypropylene (PPL), poly(styrene-co-divinylbenzene) (PSV), poly(tetrafluoroethylene) (PTF), poly(vinyl alcohol) (PVH), polyacrylamide (PAD) and poly(methyl methacrilate) (PMM).

P027 dioxane solvate may be obtained in a solvent drop grinding experiment in dioxane or by crystallization from a hot saturated solution of dioxane. P027 chloroform solvate may be obtained in polymer induced crystallizations either by solvent (chloroform) evaporation or by crystallization of hot saturated solutions of chloroform.

Thus, another embodiment of the present invention refers to a process for the preparation of solvated forms of the hydrochloride salt of 4-[2-[[5-methyl-1-(2-naphthalenyl)-

1H-pyrazol-3-yl]oxy]ethyl]morpholine, comprising at least one of the 3 alternatives i) to iii):
  i) solvent drop grinding, comprising:
    a) charging the hydrochloride salt of 4-[2-[[5-methyl-1-(2-naphthalenyl)-1H-pyrazol-3-yl]oxy]ethyl]morpholine together with catalytic quantities of a suitable solvent to a ball mill container; and
    b) grinding;
  ii) crystallization from a hot saturated solution of a suitable solvent; or
  iii) a polymer induced crystallization, comprising:
    a) dissolving the hydrochloride salt of 4-[2-[[5-methyl-1-(2-naphthalenyl)-1H-pyrazol-3-yl]oxy]ethyl]morpholine in a suitable solvent in the presence of catalytic amounts of a polymer, and
    b) either evaporating the solvent or crystallizing in a hot saturated solution of the solvent.

In a preferred embodiment, P027 dioxane solvate is prepared by:
  i) a solvent drop grinding comprising:
    a) charging the hydrochloride salt of 4-[(2-[[5-methyl-1-(2-naphthalenyl)-1H-pyrazol-3-yl]oxy]ethyl]morpholine together with catalytic quantities of dioxane to a ball mill container; and
    b) grinding; or by
  ii) crystallization from a hot saturated solution of dioxane.

In a preferred embodiment, P027 chloroform solvate is prepared by:
  a) dissolving the hydrochloride salt of 4-[(2-[[5-methyl-1-(2-naphthalenyl)-1H-pyrazol-3-yl]oxy]ethyl]morpholine in chloroform in the presence of catalytic amounts of a polymer selected from the group consisting of: poly(ethylene glycol), polyvinyl pyrrolidone, poly (acrylic acid), nylon 6/6, polypropylene, poly(tetrafluoroethylene), poly(vinyl acetate), poly(vinyl alcohol), polyacrylamide and polysulfone; and
  b) either evaporating the chloroform or crystallizing in a hot saturated solution of chloroform.

Another embodiment of the present invention includes the use of crystalline forms phase II, phase III and phase IV of P027 in the obtention of the more stable polymorphic phase I form of P027. In one embodiment, the transformation is by heating of crystalline forms phase II, phase III and phase IV into the polymorphic phase I form.

In the DSC analysis of phases II, III and IV broad exothermic peaks were observed which correspond to a solid-solid transition. The solid-solid transition (recrystallization) of phase II to phase I was observed at 145° C. The solid-solid transition (recrystallization) of phase III into phase I was observed in the range 150-170° C. The solid-solid transition (recrystallization) of phase IV into phase I was observed at 147° C.

Therefore, in another embodiment the invention is directed to the preparation of phase I form of P027 comprising the step of heating crystalline forms phase II, phase III and phase IV of P027 at a temperature between about 140° C. and about 170° C.

Another embodiment of the present invention includes the transformation of a solvate of P027, preferably chloroform solvate, into a more stable polymorphic form such as phase I form. After drying the dioxane solvate for 4 hours at 60° C., 80° C. and 100° C. the transformation to Phase I was observed. The solids obtained were characterized by PXRD.

A further embodiment of the present invention includes pharmaceutical compositions comprising at least one of the forms of the hydrochloride salt of 4-[2-[[5-methyl-1-(2-naphthalenyl)-1H-pyrazol-3-yl]oxy]ethyl]morpholine abovementioned, particularly P027 phase I, P027 phase II, P027 phase III, P027 phase IV, P027 chloroform solvate and P027 dioxane solvate, Having described the invention in general terms, it will be more easily understood by reference to the following examples which are presented as an illustration and are not intended to limit the present invention.

EXAMPLES

Equipment used in the characterization of 4-[2-[[5-methyl-1-(2-naphthalenyl)-1H-pyrazol-3-yl]oxy]ethyl]morpholine hydrochloride solid forms a) Powder X-Ray Diffraction Analysis (PXRD)

Approximately 20 mg of the non manipulated samples were prepared in standard sample holders using two foils of polyacetate.

Powder diffraction patterns were acquired on a D8 Advance Series 2Theta/Theta powder diffraction system using $Cu_{K\alpha}$-radiation in transmission geometry (Wavelength: 1.54060). The system was equipped with a VÅNTEC-1 single photon counting PSD, a Germanium monochromator, a ninety positions auto changer sample stage, fixed divergence slits and radial soller. Programs used: Data collection with DIFFRAC plus XRD Commander V.2.5.1 and evaluation with EVA V.12.0.

b) Proton Nuclear Magnetic Resonance ($^1$H NMR)

Proton nuclear magnetic resonance analyses were recorded in deuterated chloroform (CDCl3) in a Bruker Avance 400 Ultrashield NMR spectrometer, equipped with a z-gradient 5 mm BBO (Broadband Observe) probe with ATM and an automatic BACS-120 autosampler. Spectra were acquired solving 2-10 mg of sample in 0.6 mL of deuterated solvent.

c) Differential Scanning Calorimetry Analysis (DSC)

Standard DSC analyses were recorded in a Mettler Toledo DSC822e. Samples of 1-2 mg were weighted into 40 μL aluminium crucibles with a pinhole lid, and were heated, under nitrogen (50 mL/min), from 30 to 300° C. at 10° C./min. Data collection and evaluation was done with software STARe.

d) Thermogravimetric Analysis (TGA)

Thermogravimetric analyses were recorded in a Mettler Toledo SDTA851e. Samples of 3-4 mg were weighted (using a microscale MX5, Mettler) into open 40 μL aluminium crucibles with a pinhole lid, and heated at 10° C./min between 30 and 500° C., under nitrogen (80 mL/min). Data collection and evaluation was done with software STARe.

e) Fourier Transform Infrared Analysis (FTIR)

The FTIR spectra were recorded using a Bruker Tensor 27, equipped with a MKII golden gate single reflection ATR system, a mid-infrared source as the excitation source and a DTGS detector. The spectra were acquired in 32 scans at a resolution of 4 $cm^{-1}$. No sample preparation was required to perform the analysis.

f) Single Crystal X-Ray Diffraction Analysis (SCXRD)

The measured crystals were selected using a Zeiss stereomicroscope using polarized light and prepared under inert conditions immersed in perfluoropolyether as protecting oil for manipulation. Crystal structure determination was carried out using a Bruker-Nonius diffractometer equipped with a APPEX 2 4K CCD area detector, a FR591 rotating anode with MoKα radiation, Montel mirrors as monochromator and a Kryoflex low temperature device (T=100 K). Fullsphere data collection omega and phi scans. Programs used: Data collection Apex2 V. 1.0-22 (Bruker-Nonius 2004), data reduction Saint+Version 6.22 (Bruker-Nonius 2001) and absorption correction SADABS V. 2.10 (2003). Crystal structure solution was achieved using direct methods as implemented in SHELXTL Version 6.10 (Sheldrick, Universtität Göttingen (Germany), 2000) and visualized using XP program. Missing atoms were subsequently located from difference Fourier synthesis and added to the atom list. Least-squares refinement on $F_0^2$ using all measured intensities was carried out using the program SHELXTL Version 6.10 (Sheldrick, Universtität Göttingen (Germany), 2000). All non hydrogen atoms were refined including anisotropic displacement parameters.

Initial Synthesis of the P027 Compound

4-[2-[[5-methyl-1-(2-naphthalenyl)-1H-pyrazol-3-yl] oxy]ethyl]morpholine hydrochloride was obtained according to the following protocols:

1) 50.8 liters of a 6N hydrochloric acid/propan-2-ol solution was added to a solution of 4-[2-[[5-methyl-1-(2-naphthalenyl)-1H-pyrazol-3-yl]oxy]ethyl]morpholine (85 kg) in ethanol (290 l) at T>35° C. Then, 213 liters of methyl tert-butyl ether was added to the suspension. The mixture was cooled later at 0-5° C. The resulting solid was isolated by centrifugation to yield 90 kg of the P027 compound.

2) 27 ml of a 6N hydrochloric acid/propan-2-ol solution was added to a solution of 4-[2-[[5-methyl-1-(2-naphthalenyl)-1H-pyrazol-3-yl]oxy]ethyl]morpholine (44.5 g) in ethanol (120 mL) and methyl tert-butyl ether (112 mL) at T>35° C. Next, the suspension was cooled at 0-5° C. The resulting solid was isolated by filtration to yield 47 g of the P027 compound.

Example 1

Preparation and characterization of 4-[2-[[5-methyl-1-(2-naphthalenyl)-1H-pyrazol-3-yl]oxy]ethyl]morpholine hydrochloride phase I crystalline form Example 1.1

Solvent Evaporation at Two Rates at Room Temperature

Between 10 to 20 mg of the P027 compound were dissolved in the minimum amount of the relevant solvents at room temperature (rt), at 60° C. and 80° C. The resulting solutions were left to evaporate rapidly in open vials or slowly in closed tubes pierced with a needle at room temperature (see Tables 9 and 10). Those solutions which were not completely evaporated after 3 months were allowed to evaporate at room temperature in open vials. The solid samples obtained were analyzed by PXRD. The samples showed a pattern consistent with the standard PXRD phase I pattern.

TABLE 9

Fast solvent evaporation at room temperature

| Solvent | V (mL) | Dissolution temperature |
|---------|--------|-------------------------|
| ACE | 2.5 | rt |
| ACN | 0.8 | 60° C. |
| BUL | 3.2 | 60° C. |
| CDM | 8.0 | 80° C. |
| CLF | 0.2 | rt |
| DCE | 0.6 | rt |
| DCM | 0.2 | rt |
| DIX | 7.0 | 80° C. |
| DMF | 0.2 | rt |
| EOH | 0.6 | rt |
| H2O | 0.2 | rt |

TABLE 9-continued

Fast solvent evaporation at room temperature

| Solvent | V (mL) | Dissolution temperature |
|---------|--------|-------------------------|
| IPH | 2.5 | 60° C. |
| MEC | 3.5 | 60° C. |
| MOH | 0.2 | rt |
| NBL | 1.4 | 60° C. |
| NIM | 0.4 | rt |
| PYR | 0.4 | rt |

TABLE 10

Slow solvent evaporation at room temperature

| Solvent | V (mL) | Dissolution temperature |
|---------|--------|-------------------------|
| ACE | 2.5 | rt |
| ACN | 0.8 | 60° C. |
| CDM | 8.0 | 80° C. |
| CLF | 0.2 | rt |
| DCE | 0.6 | rt |
| DCM | 0.2 | rt |
| DMF | 0.2 | rt |
| EOH | 0.6 | rt |
| H2O | 0.2 | rt |
| IPH | 2.5 | 60° C. |
| MEC | 3.5 | 60° C. |
| NIM | 0.4 | rt |
| PYR | 0.4 | rt |

Example 1.2

Solvent Evaporation at Different Temperatures

Figure 14:
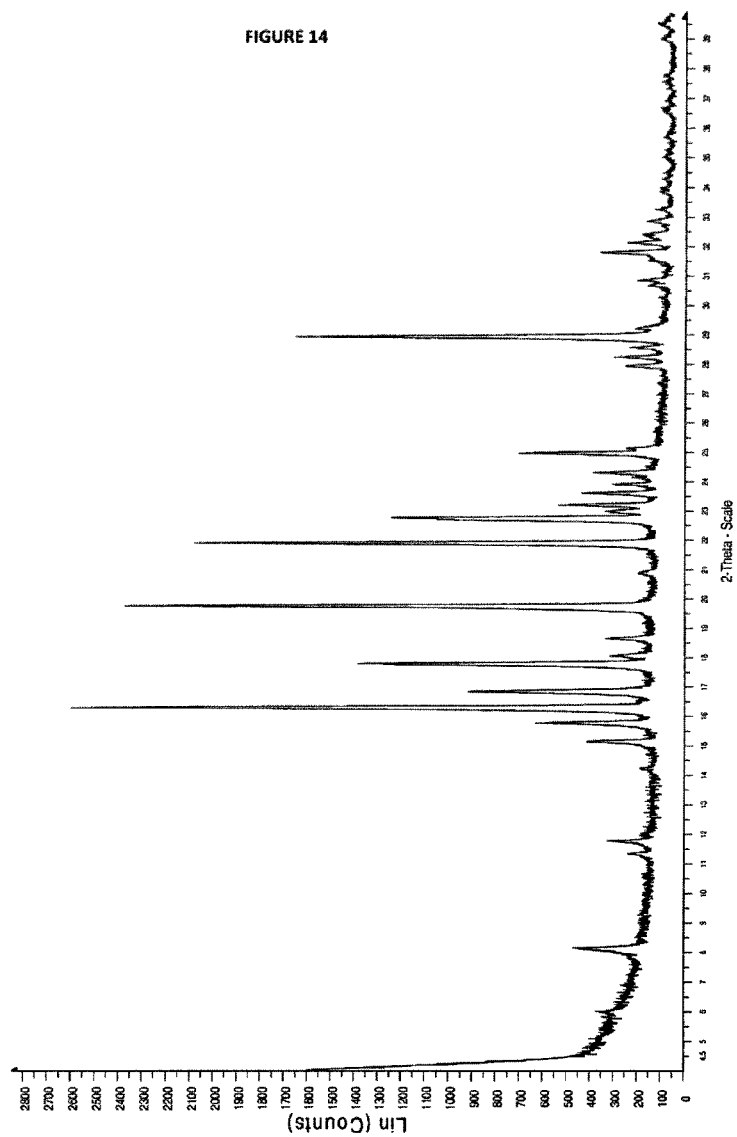
FIG. 14: PXRD pattern of a phase I form obtained by the evaporation n-butanol at −21° C.

Between 10 to 20 mg of the P027 compound were dissolved in the minimum amount of the relevant solvents at room temperature (rt), at 60° C. or at 80° C. The resulting solutions were left to evaporate, in open vials, at three different temperatures: 60° C., 4° C. and −21° C. (see Tables 11, 12 and 13). Those solutions which were not completely evaporated after 3 months were allowed to evaporate at room temperature in open vials. The solid samples obtained were analyzed by PXRD. The samples showed a pattern consistent with the standard PXRD phase I pattern. FIG. 14 illustrates the PXRD pattern of a phase I form obtained by the evaporation of a n-butanol solution at −21° C. according to the present protocol.

TABLE 11

Solvent evaporation at 60° C.

| Solvent | V (mL) | Dissolution temperature |
|---------|--------|-------------------------|
| ACE | 2.5 | rt |
| ACN | 0.8 | 60° C. |
| BUL | 3.2 | 60° C. |
| CDM | 8.0 | 80° C. |
| CLF | 0.2 | rt |
| DCE | 0.6 | rt |
| DCM | 0.2 | rt |
| DIX | 7.0 | 80° C. |
| DMA | 0.4 | rt |
| DMF | 0.2 | rt |
| DMS | 0.2 | rt |
| EOH | 0.6 | rt |
| H2O | 0.2 | rt |
| IPH | 2.5 | 60° C. |
| MEC | 3.5 | 60° C. |
| MOH | 0.2 | rt |

TABLE 11-continued

Solvent evaporation at 60° C.

| Solvent | V (mL) | Dissolution temperature |
|---------|--------|-------------------------|
| NBL | 1.4 | 60° C. |
| NIM | 0.4 | rt |
| POA | 6.0 | 80° C. |
| PYR | 0.4 | rt |

TABLE 12

Solvent evaporation at 4° C.

| Solvent | V (mL) | Dissolution temperature |
|---------|--------|-------------------------|
| ACE | 2.5 | rt |
| ACN | 0.8 | 60° C. |
| CLF | 0.2 | rt |
| DCE | 0.6 | rt |
| DCM | 0.2 | rt |
| DIX[1] | 7.0 | 80° C. |
| DMF[1] | 0.2 | rt |
| EOH | 0.6 | rt |
| IPH | 2.5 | 60° C. |
| MEC | 3.5 | 60° C. |
| MOH | 0.2 | rt |
| NBL[1] | 1.4 | 60° C. |
| NIM | 0.4 | rt |
| POA[1] | 6.0 | 80° C. |
| PYR | 0.4 | rt |

[1] The solution was left to evaporate in an open vial at room temperature.

TABLE 13

Solvent evaporation at −21° C.

| Solvent | V (mL) | Dissolution temperature |
|---------|--------|-------------------------|
| ACE | 2.5 | rt |
| ACN | 0.8 | 60° C. |
| BUL | 3.2 | 60° C. |
| CLF | 0.2 | rt |
| DCE | 0.6 | rt |
| DCM | 0.2 | rt |
| DMF | 0.2 | rt |
| EOH[1] | 0.6 | rt |
| IPH | 2.5 | 60° C. |
| MEC[1] | 3.5 | 60° C. |
| MOH | 0.2 | rt |
| NBL | 1.4 | 60° C. |
| NIM | 0.4 | rt |
| PYR[1] | 0.4 | rt |

[1] The solution was left to evaporate in an open vial at room temperature.

Example 1.3

Crystallization from Hot Saturated Solutions

Between 20 to 30 mg of the P027 compound were dissolved in the minimum amount of the relevant solvents at high temperature to obtain saturated solutions. The solutions were then cooled by two different methods:

1) Slow cool down at room temperature (slow crystallization) [see Table 14].
2) Rapid cool down by ice bath immersion (fast crystallization) [see Table 15].

After cooling at room temperature the solids obtained were separated by filtration or centrifugation. If no solids were formed, the solution was kept at 4° C. for a few days in first step. Any solids formed during this step were separated from the solution. If no solids were formed during the first step, the solution was kept at −21° C. for a few additional days. Any solids formed during this second step were separated from the solution. The solutions that did not crystallize during the second step were left to evaporate to dryness at room temperature. The solid was filtered off in some experiments when crystallization occurred before complete evaporation.

Figure 15:
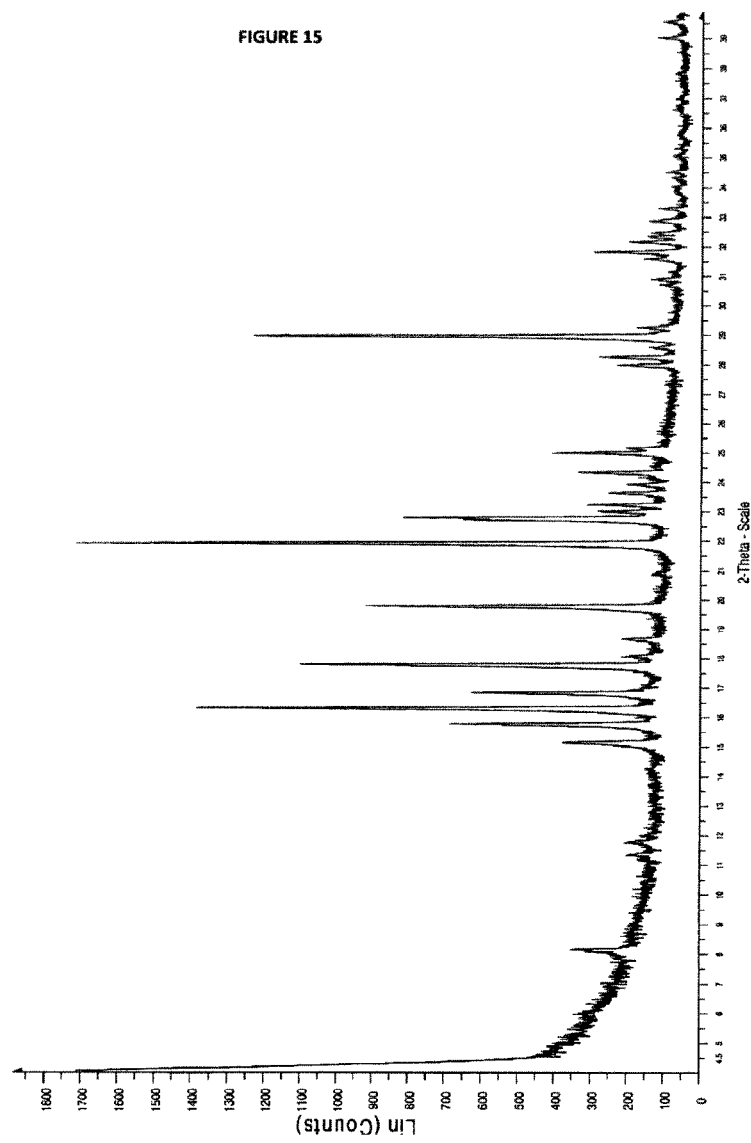
FIG. 15: PXRD pattern of a phase I form obtained by the slow crystallization of hot saturated P027 compound solution in methyl ethyl ketone.

The solid samples obtained were analyzed by PXRD. The samples showed a pattern consistent with the standard PXRD phase I pattern. FIG. 15 illustrates the PXRD pattern of a phase I form obtained by the slow crystallization of hot saturated P027 compound solution in methyl ethyl ketone.

TABLE 14

Slow crystallization from hot saturated solutions

| Solvent | V (mL) | Dissolution temperature | Crystallization conditions |
|---------|--------|-------------------------|----------------------------|
| ACE | 3.7 | 56° C. | at −21° C. |
| ACN | 0.6 | 80° C. | at rt |
| BUL | 0.4 | 98° C. | at rt |
| CLF | 0.2 | rt | Evaporation |
| DCE | 0.4 | 80° C. | at rt |
| DCM | 0.4 | 40° C. | Evaporation |
| DIX | 1.0 | 101° C. | at rt |
| DMA | 0.2 | 100° C. | at −21° C. |
| DMF | 0.2 | 100° C. | Evaporation |
| EOH | 0.4 | 78° C. | at rt |
| H2O | 0.2 | 100° C. | Evaporation |
| IPH | 0.6 | 80° C. | at rt |
| MEC | 2.7 | 80° C. | at 4° C. |
| MOH | 0.2 | 56° C. | at −21° C. |
| NBL | 0.4 | 118° C. | at rt |
| NIM | 0.4 | 101° C. | at −21° C. |
| PYR | 0.2 | rt | Evaporation |

TABLE 15

Fast crystallization from hot saturated solutions

| Solvent | V (mL) | Dissolution temperature | Crystallization conditions |
|---------|--------|-------------------------|----------------------------|
| ACE | 4.0 | 56° C. | Immediately |
| ACN | 0.6 | 80° C. | at −21° C. |
| BUL | 0.4 | 98° C. | Immediately |
| CLF | 0.2 | rt | Evaporation |
| DCE | 0.4 | 80° C. | at −21° C. |
| DCM | 0.4 | 40° C. | at −21° C. |
| DIX | 1.0 | 101° C. | Immediately |
| DMA | 0.2 | 100° C. | Evaporation |
| DMF | 0.2 | 100° C. | Evaporation |
| EOH | 0.4 | 78° C. | at −21° C. |
| H2O | 0.2 | rt | Evaporation |
| IPH | 0.6 | 80° C. | at −21° C. |
| MEC | 2.7 | 80° C. | at −21° C. |
| MOH | 0.2 | 56° C. | at −21° C. |
| NBL | 0.4 | 118° C. | Immediately |
| NIM | 0.4 | 101° C. | Immediately |
| PYR | 0.2 | rt | Immediately |

Example 1.4

Small Scale Crystallization by Addition of an Antisolvent

Between 10 to 20 mg of the P027 compound were dissolved in the minimum amount of the relevant dissolving agent at high temperature or at room temperature. Diisopropyl ether (DIE) and n-heptane (HEP) were used as antisolvents. The following protocols were performed:

1) The antisolvent was added drop-wise to a P027 solution under vigorous stirring at room temperature or at high temperature (see Tables 16 and 17).
2) A P027 solution was added drop wise to 4 mL of the antisolvent under vigorous stirring at room temperature or at high temperature (see Tables 18 and 19).

The solids obtained after mixing the dissolving agent and antisolvent were separated from the solution by filtration or centrifugation. If no solids were formed, the solution was kept at 4° C. for a few days in first step. Any solids formed during this step were separated from the solution. If no solids were formed during the first step, the solution was kept at −21° C. for a few additional days. Any solids formed during this second step were separated from the solution. The solutions that did not crystallize during the second step were left to evaporate to dryness at room temperature. The solid was filtered off in some experiments when crystallization occurred before complete evaporation.

Figure 16:
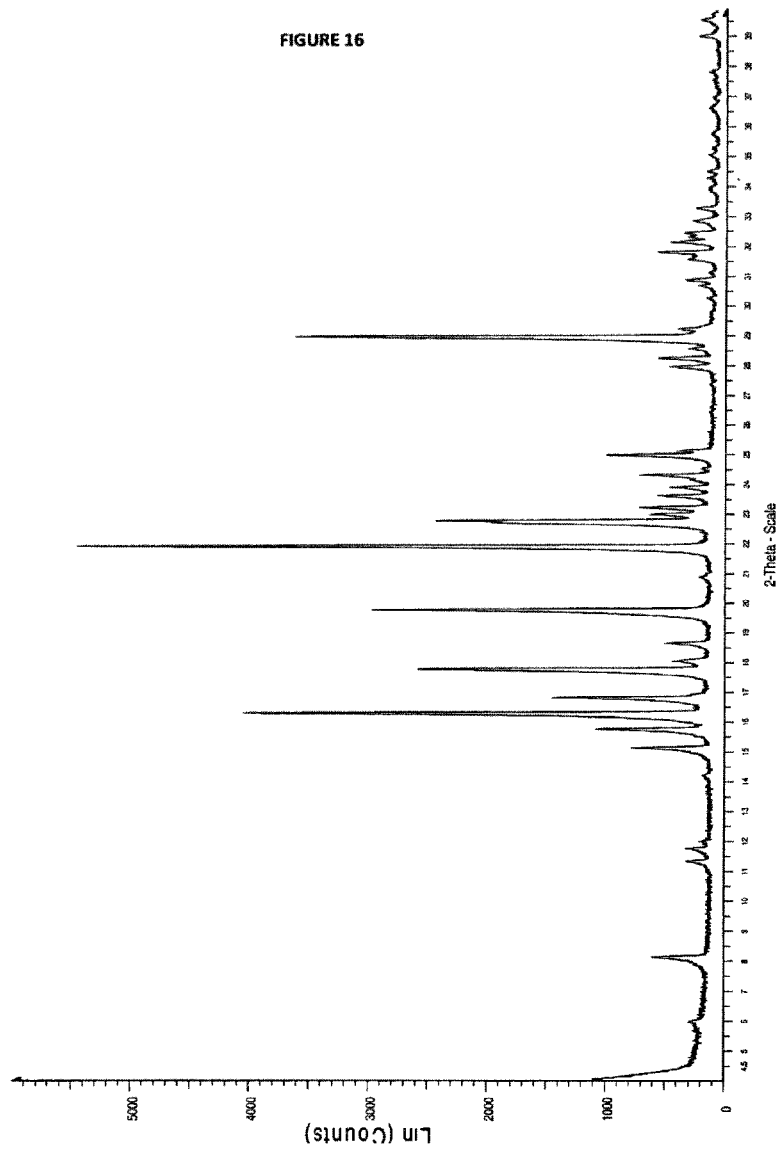
FIG. 16: PXRD pattern of a phase I form obtained by crystallization through the addition of a P027 solution in methanol to an n-heptane solution.

The solid samples obtained were analyzed by PXRD. The samples showed a pattern consistent with the standard PXRD phase I pattern. FIG. 16 illustrates the PXRD pattern of a phase I form obtained by crystallization through the addition of a P027 solution in methanol to an n-heptane solution.

TABLE 16

Crystallization by the addition of an antisolvent to a P027 solution at room temperature

| Dissolving Solvent | Anti-solvent | Crystallization conditions |
|---|---|---|
| ACE | DIE | at −21° C. |
|  | HEP | Evaporation |
| ACN | DIE | Immediately |
|  | HEP[1] | at 4° C. |
| BUL | DIE[1] | Immediately |
|  | HEP[1] | Immediately |
| CLF | DIE | Immediately |
|  | HEP | Immediately |
| DCE | DIE | Immediately |
|  | HEP | Immediately |
| DCM | DIE | Immediately |
|  | HEP | Immediately |
| DIX | DIE[1] | Immediately |
|  | HEP | Immediately |
| DMA | DIE | Immediately |
|  | HEP[1] | Evaporation |
| EOH | DIE | Immediately |
|  | HEP | Immediately |
| IPH | DIE | at 4° C. |
|  | HEP | at 4° C. |
| MEC | DIE | Immediately |
|  | HEP | Immediately |
| MOH | DIE | Immediately |
|  | HEP[1] | Immediately |
| NBL | DIE | Immediately |
|  | HEP[1] | Immediately |
| NIM | DIE | Immediately |
|  | HEP | Evaporation |
| PYR | DIE | Immediately |
|  | HEP | Immediately |

[1]Solvent and antisolvent were immiscible.

TABLE 17

Crystallization by the addition of an antisolvent to a P027 solution at high temperature

| Dissolving solvent | T (° C.) | Anti-solvent | Crystallization conditions |
|---|---|---|---|
| ACN | 65 | DIE | Immediately |
|  | 80 | HEP | at −21° C. |
| BUL | 65 | DIE | Immediately |
|  | 90 | HEP | Immediately |
| CLF | 60 | DIE | Immediately |
|  | 60 | HEP | Immediately |
| DCE | 65 | DIE | Immediately |
|  | 80 | HEP | Immediately |
| DCM | 40 | DIE | Immediately |
|  | 40 | HEP | Immediately |
| DIX | 65 | DIE | Immediately |
|  | 90 | HEP | at −21° C. |
| DMA | 65 | DIE | Immediately |
|  | 90 | HEP | Evaporation |
| EOH | 65 | DIE | Immediately |
|  | 75 | HEP | Immediately |
| IPH | 65 | DIE | at −21° C. |
|  | 80 | HEP | at −21° C. |
| MEC | 65 | DIE | Immediately |
|  | 80 | HEP | Immediately |
| MOH | 65 | DIE | Immediately |
|  | 65 | HEP | Immediately |
| NBL | 65 | DIE | Immediately |
|  | 90 | HEP | Immediately |
| NIM | 65 | DIE | Immediately |
|  | 90 | HEP | Evaporation |

TABLE 18

Crystallization by the addition of a P027 solution to an antisolvent at room temperature

| Dissolving solvent | Anti-solvent | Crystallization conditions |
|---|---|---|
| ACE | DIE | Immediately |
|  | HEP | Immediately |
| ACN | DIE | Immediately |
|  | HEP[1] | Immediately |
| BUL | DIE | Immediately |
|  | HEP | Immediately |
| CLF | DIE | Immediately |
|  | HEP | Immediately |
| DCE | DIE | Immediately |
|  | HEP | Immediately |
| DCM | DIE | Immediately |
|  | HEP | Immediately |
| DIX | DIE | Immediately |
|  | HEP | Immediately |
| DMA | DIE | Immediately |
|  | HEP[1] | Immediately |
| EOH | DIE | Immediately |
|  | HEP | Immediately |
| IPH | DIE | Immediately |
|  | HEP | Immediately |
| MEC | DIE | Immediately |
|  | HEP | Immediately |
| MOH | DIE | Immediately |
|  | HEP[1] | Evaporation |
| NBL | DIE | Immediately |
|  | HEP[1] | Immediately |
| NIM | DIE | Immediately |
|  | HEP[1] | Evaporation |

[1]Solvent and antisolvent were immiscible.

TABLE 19

Crystallization by the addition of a P027 solution to an antisolvent at high temperature

| Dissolving solvent | T (° C.) | Anti-solvent | Crystallization conditions |
|---|---|---|---|
| ACE | 55 | DIE | Immediately |
|  | 55 | HEP | Immediately |
| ACN | 65 | DIE | Immediately |
|  | 80 | HEP[1] | at 4° C. |
| BUL | 65 | DIE | at 4° C. |
|  | 90 | HEP | Immediately |
| CLF | 60 | DIE | Immediately |
|  | 60 | HEP | Immediately |
| DCE | 65 | DIE | Immediately |
|  | 80 | HEP | Immediately |
| DCM | 40 | DIE | Immediately |
|  | 40 | HEP | Immediately |
| DMA | 65 | DIE | Immediately |
|  | 90 | HEP | Immediately |
| EOH | 65 | DIE | Immediately |
|  | 75 | HEP | Immediately |
| IPH | 65 | DIE | at 4° C. |
|  | 80 | HEP | Immediately |
| MEC | 65 | DIE | Immediately |
|  | 80 | HEP | Immediately |
| MOH | 65 | DIE | Immediately |
|  | 65 | HEP[1] | Evaporation |
| NBL | 65 | DIE | at 4° C. |
|  | 90 | HEP | Immediately |
| NIM | 65 | DIE | Immediately |
|  | 90 | HEP[1] | Evaporation |

[1]Solvent and antisolvent were immiscible.

Example 1.5

Large Scale Crystallization by Addition of an Antisolvent 133 liters of methyl tert-butyl ether was added to a P027 compound (45 kg) in ethanol (265 l) solution of at T>35° C. Next, the suspension was cooled at 0-5° C. The resulting solid was isolated by centrifugation to yield 40.2 kg of 4-[2-[[5-methyl-1-(2-naphthalenyl)-1H-pyrazol-3-yl]oxy]ethyl]morpholine hydrochloride.

Example 1.6

Crystallization by Diffusion of an Antisolvent

Between 10 to 50 mg of the P027 compound were dissolved in the minimum amount of the relevant solvents at high temperature or at room temperature. Various dissolving agents were utilized. The following protocols were performed:
1) Liquid-liquid diffusion. The antisolvent was added carefully over a P027 solution forming two separated phases. The solid crystallized due to the diffusion of the phases (see Table 20).
2) Gas-liquid diffusion. A first container with a P027 solution was inserted into a second larger recipient containing the antisolvent. The gas diffusion of the antisolvent over the P027 solution induced the crystallization of phase I (see Table 21).

Figure 17:
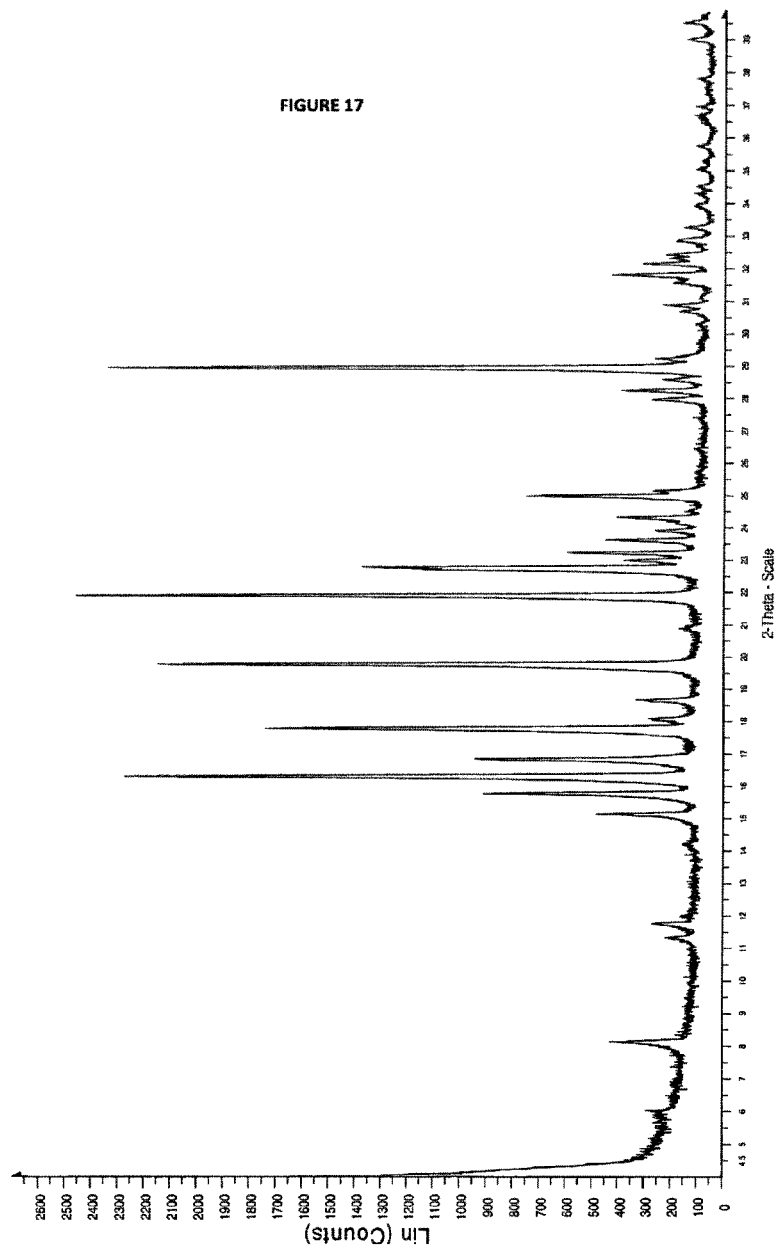
FIG. 17: PXRD pattern of a phase I form obtained by crystallization through a liquid-liquid diffusion of a P027 solution in nitromethane and an isopropyl ether solution.

The solid samples obtained were analyzed by PXRD. The samples showed a pattern consistent with the standard PXRD phase I pattern. FIG. 17 illustrates the PXRD pattern of a phase I form obtained by crystallization through a liquid-liquid diffusion of isopropyl ether into a P027 solution in nitromethane.

TABLE 20

Crystallization by liquid-liquid diffusion

| Dissolving solvent | V Solvent (mL)[1] | Anti-solvent | Crystallization conditions |
|---|---|---|---|
| ACN | 0.8 | DIE | Crystallization |
|  |  | HEP | Crystallization |
| CLF | 1 | DIE | Crystallization |
|  |  | HEP | Crystallization |
| DCE | 1.2 | DIE | Crystallization |
|  |  | HEP | Crystallization |
| DCM | 1 | DIE | Crystallization |
|  |  | HEP | Crystallization |
| EOH | 1.2 | DIE | Crystallization |
|  |  | HEP | Crystallization |
| IPH | 2.5 | DIE | Evaporation |
|  |  | HEP | Crystallization |
| MOH | 1 | DIE | Evaporation |
|  |  | HEP | Evaporation |
| NIM | 1 | DIE | Evaporation |
|  |  | HEP | Evaporation |
| PYR | 1 | DIE | Evaporation |
|  |  | HEP | Crystallization |

[1]Equal quantities of dissolving solvent and antisolvent were added.

TABLE 21

Crystallization by gas-liquid diffusion

| Dissolving solvent | Anti-solvent | Crystallization conditions |
|---|---|---|
| ACN | HEP | Evaporation |
|  | DIE | Crystallization |
| CLF | HEP | Crystallization |
|  | DIE | Crystallization |
| DCE | HEP | Crystallization |
|  | DIE | Crystallization |
| DCM | HEP | Crystallization |
|  | DIE | Crystallization |
| DMF | HEP | Crystallization |
|  | DIE | Crystallization |
| EOH | HEP | Crystallization |
|  | DIE | Crystallization |
| MOH | HEP | Crystallization |
|  | DIE | Crystallization |
| NIM | HEP | Evaporation |
|  | DIE | Evaporation |
| PYR | HEP | Crystallization |
|  | DIE | Crystallization |

Example 1.7

Crystallization from Mixtures of Water and Solvent

Between 10 to 20 mg of the P027 compound were dissolved in the minimum amount of the relevant solvent saturated with water. The solvents were mixed at various ratios with water according to their miscibility (see Table 22).

The solutions were allowed to crystallize at room temperature in a closed tube for two weeks. If no solids were formed, the solution was kept at 4° C. for a few days. Any solids formed during this step were separated from the solution. If no solids were formed during the first step, the solution was left to evaporate to dryness at room temperature.

The solid samples obtained were analyzed by PXRD. The samples showed a pattern consistent with the standard PXRD phase I pattern.

TABLE 22

Crystallization from mixtures of water and solvent

| Solvent | V (mL) | Dissolution Temperature (° C.) | Water saturation | Observations |
|---|---|---|---|---|
| ACN | 0.2 | 60 | 50% | Evaporation |
|  | 0.2 | 60 | 75% | Evaporation |
| CLF | 0.9 | 60 | 0.2% | Evaporation |
| DCE | 0.4 | 70 | 0.15% | Evaporation |
| DCM | 0.4 | 40 | 0.15% | Evaporation |
| DIX | 0.2 | 60 | 50% | Evaporation |
|  | 0.2 | 60 | 75% | Evaporation |
| IPH | 0.2 | 60 | 25% | Evaporation |
|  | 0.2 | 60 | 50% | Evaporation |
| MEC | 0.2 | 60 | 10% | Evaporation |
| MOH | 0.2 | 60 | 25% | Evaporation |
| NBL | 0.2 | 60 | 15% | Crystallization |

Example 1.8

Grinding

Approximately 40 mg of P027 phase I were transferred to a ball mill container together with catalytic quantities of the relevant solvent (three drops). The P027 phase I and the solvent were grinded at a maximum frequency of 30 s$^{-1}$ for 30 minutes (see Table 23).

Figure 18:
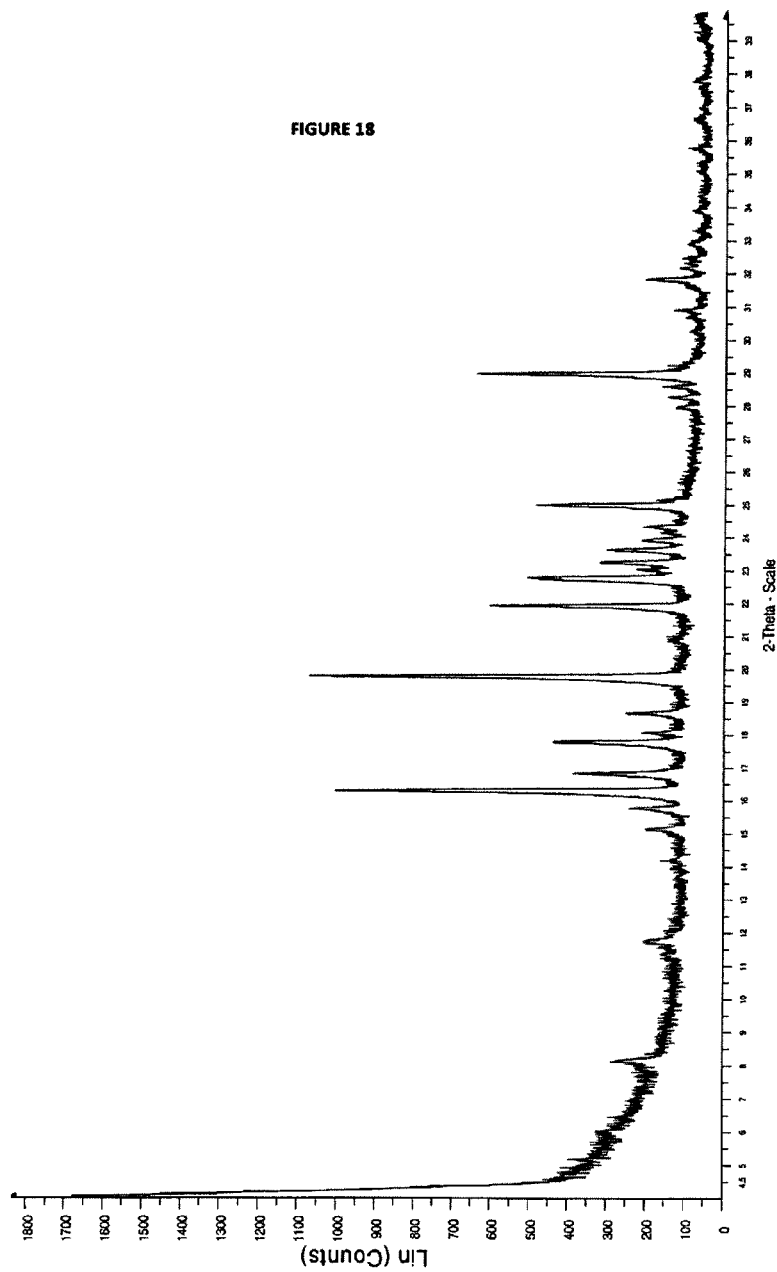
FIG. 18: PXRD pattern obtained after grinding a sample of P027 phase I form together with dichloromethane. The pattern is consistent with the standard phase I PXRD pattern demonstrating the phase stability.

The solid samples obtained were analyzed by PXRD. The samples showed a pattern consistent with the standard PXRD phase I pattern, thus demonstrating that P027 phase I is stable after grinding. FIG. 18 illustrates the PXRD pattern of a phase I form obtained from grinding P027 together with dichloromethane.

TABLE 23

Solvents utilized in grinding assays

| ACE | DCE | EOH | NIM |
|---|---|---|---|
| ACN | DCM | IPH | POA |
| BUL | DMA | MEC | PYR |
| CDM | DMF | MOH | THF |
| CLF | DMS | NBL |  |

Example 1.9

Pressure

Tablets of P027 phase I were prepared in a hydraulic press at three different pressures (5, 7.5 and 10 tons) for three different times (5, 30 and 90 minutes) [see Table 24].

Figure 19:
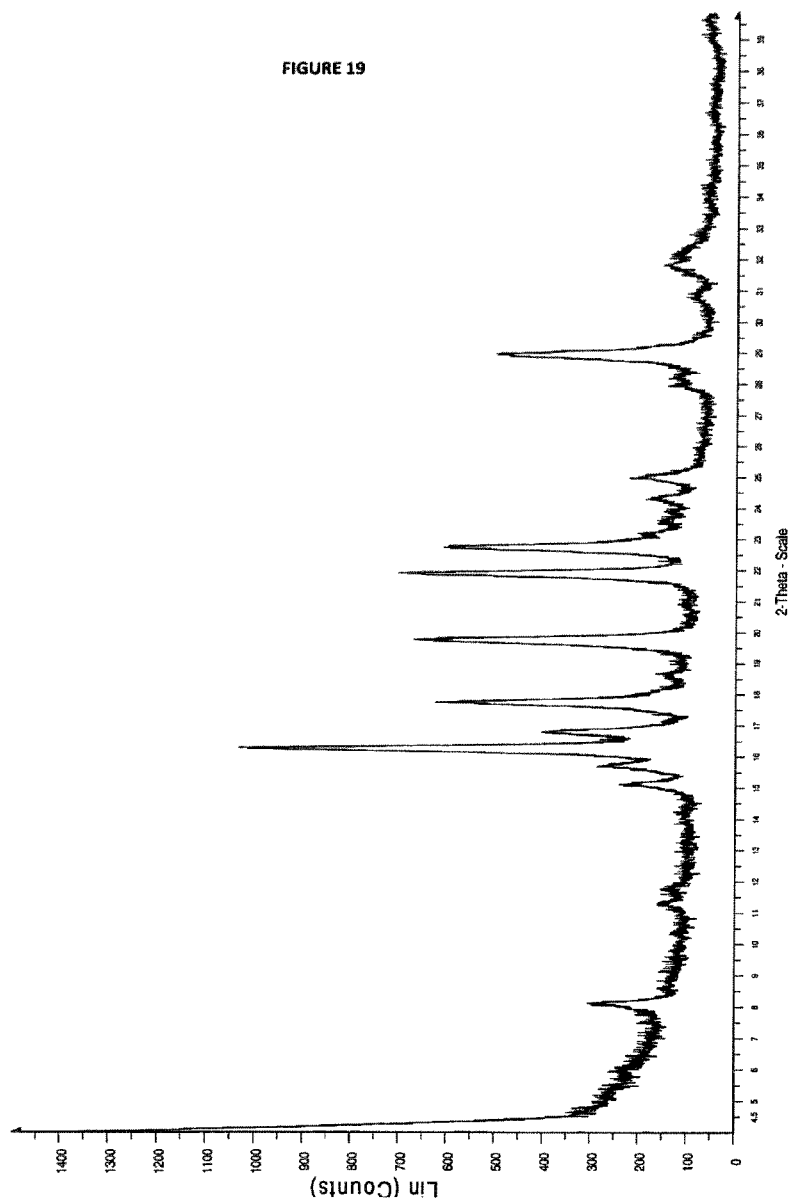
FIG. 19: PXRD pattern of a sample of P027 phase I form after applying a pressure of 30 tons to the sample for 90 minutes. The pattern is consistent with the standard phase I PXRD pattern demonstrating the phase stability.
Figure 20:
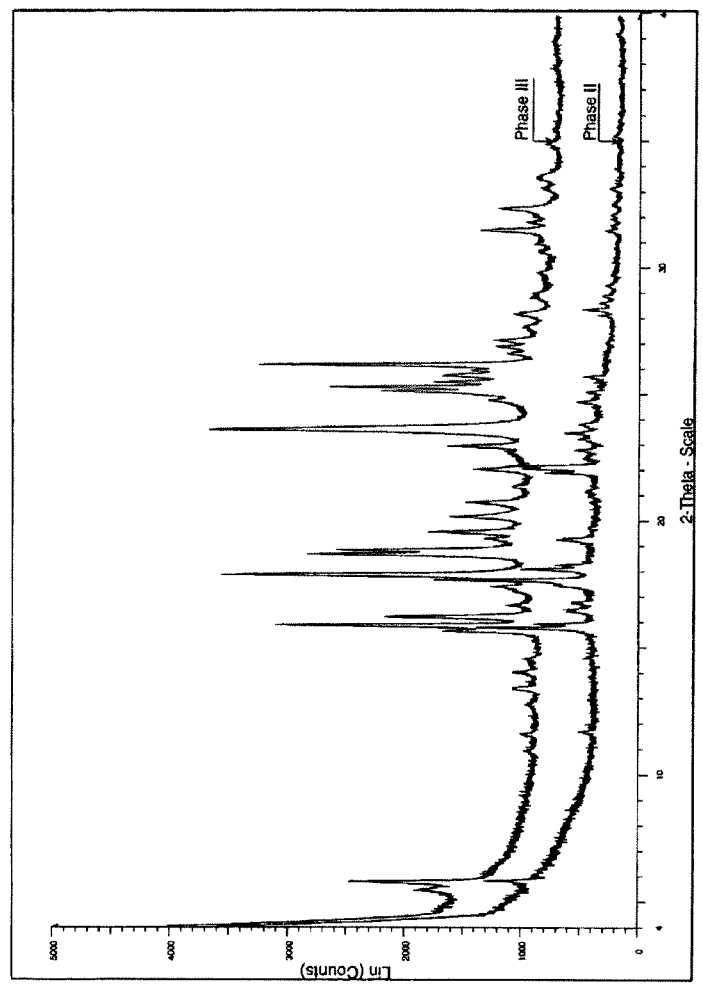
FIG. 20: Comparison of the PXRD patterns obtained for Phase II and Phase III.
Figure 21:
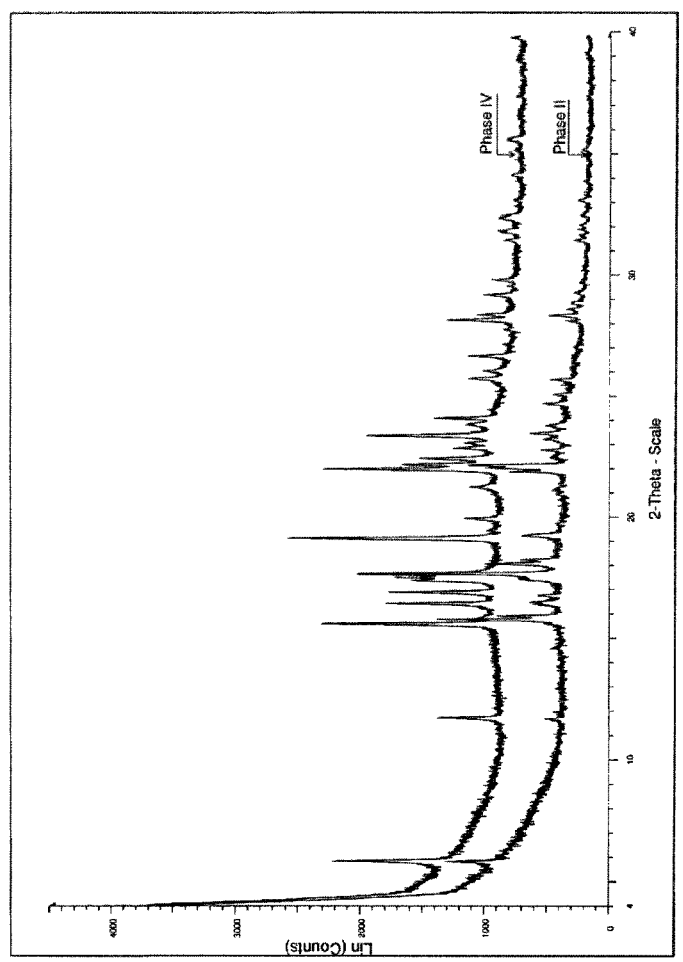
FIG. 21: Comparison of the PXRD patterns obtained for Phase II and Phase IV.
Figure 22:
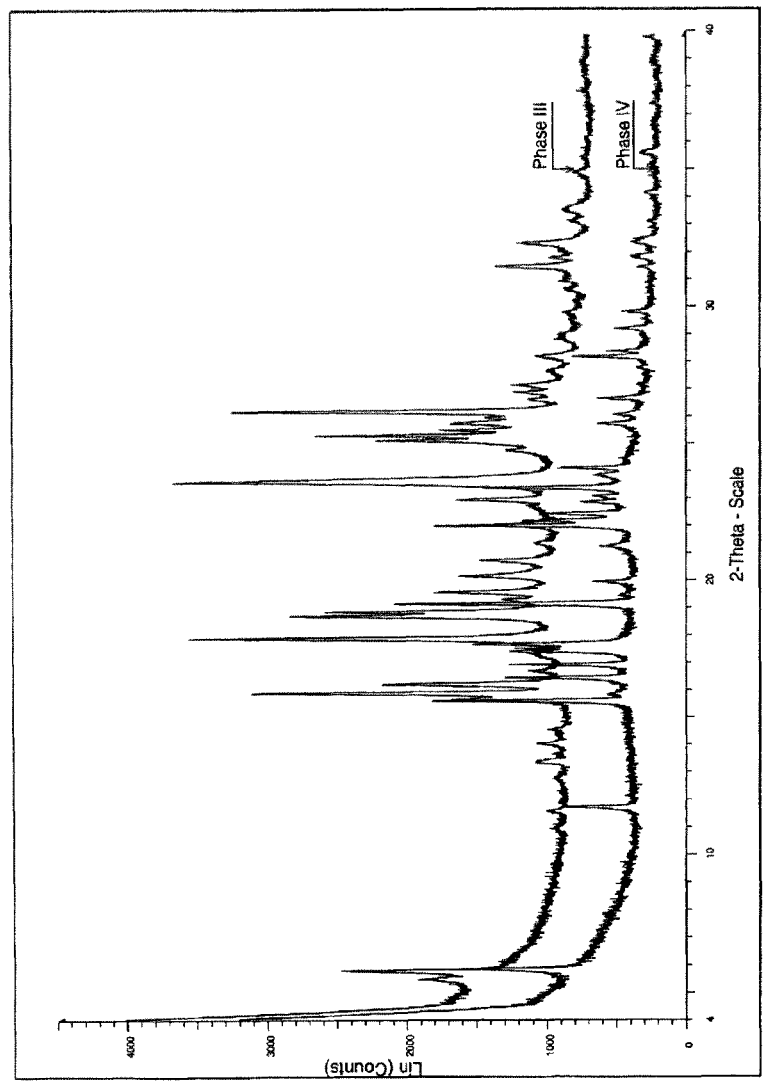
FIG. 22: Comparison of the PXRD patterns obtained for Phase III and Phase IV.

The solid samples obtained were analyzed by PXRD. The samples showed a pattern consistent with the standard PXRD phase I pattern, thus demonstrating that P027 phase I is stable under pressure. FIG. 19 illustrates the PXRD pattern of a phase I form obtained by applying a pressure of 30 tons to P027 for 90 minutes.

TABLE 24

Pressure parameters

| Pressure (Tons) | Time (min) |
|---|---|
| 5 | 5 |
| 5 | 30 |
| 5 | 90 |
| 7.5 | 5 |
| 7.5 | 30 |
| 7.5 | 90 |
| 10 | 5 |
| 10 | 30 |
| 10 | 90 |

Example 1.10

Preparation of Suspensions

Between 30 to 400 mg of the P027 compound were stirred in 4 mL of the relevant solvent for: i) 48 hours at room temperature or ii) 24 hours at 80° C. (see Table 25).

All suspensions were filtered. The solid samples obtained were analyzed by PXRD. The samples showed a pattern consistent with the standard PXRD phase I pattern.

TABLE 25

Slurry suspensions

| Solvent | T (° C.) |
|---|---|
| DIE | rt |
|  | 65 |
| HEP | rt |
|  | 80 |
| TCE | rt |
|  | 70 |

Characterization of 4-[2-[[5-methyl-1-(2-naphthalenyl)-1H-pyrazol-3-yl]oxy]ethyl]morpholine hydrochloride phase I crystalline form The P027 phase I form shows a PXRD pattern having characteristic peaks at a reflection angle [2θ] of about 5.9, 8.1, 11.3, 11.7, 14.2, 15.1, 15.8, 16.3, 16.8, 17.8, 18.1, 18.6, 19.8, 20.9, 21.9, 22.8, 23.0, 23.2, 23.6, 23.9, 24.3, 25.0, 25.1, 28.0, 28.3, 28.6, 29.0, 29.2, 30.7, and 30.9 with the 2θ values being obtained using copper radiation (Cu$_{K\alpha1}$ 1.54060 Å).

Figure 5:
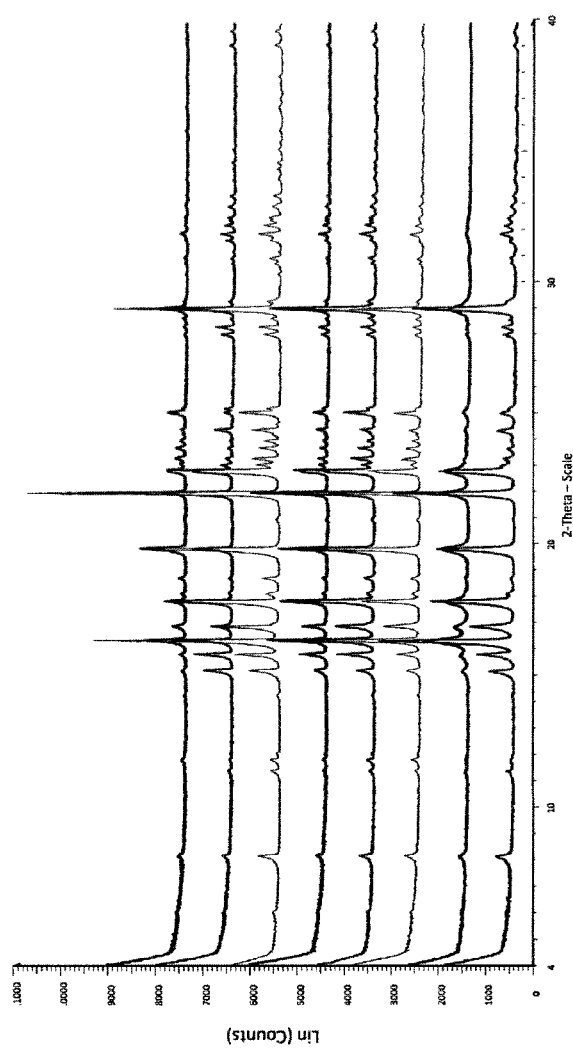
FIG. 5: Randomly selected PXRD patterns of different solids corresponding to phase I in which texture effects can be observed.

Differences in the PXRD patterns peak intensities could be observed depending of the crystallization procedure or crystallization solvent used (see FIG. 5). Strong differences in the peak intensities could be due to preferred orientations, texture effects, of the crystals and are not indicative of the presence of different crystalline phases. Non ideal crystalline phases are defined by the peak positions and not by the peak intensities. Differences in the peak intensities could be due to different configurations of the measurement devices (transmission vs. reflection) or to texture effects related to the preferred orientations of the crystals.

Figure 6:
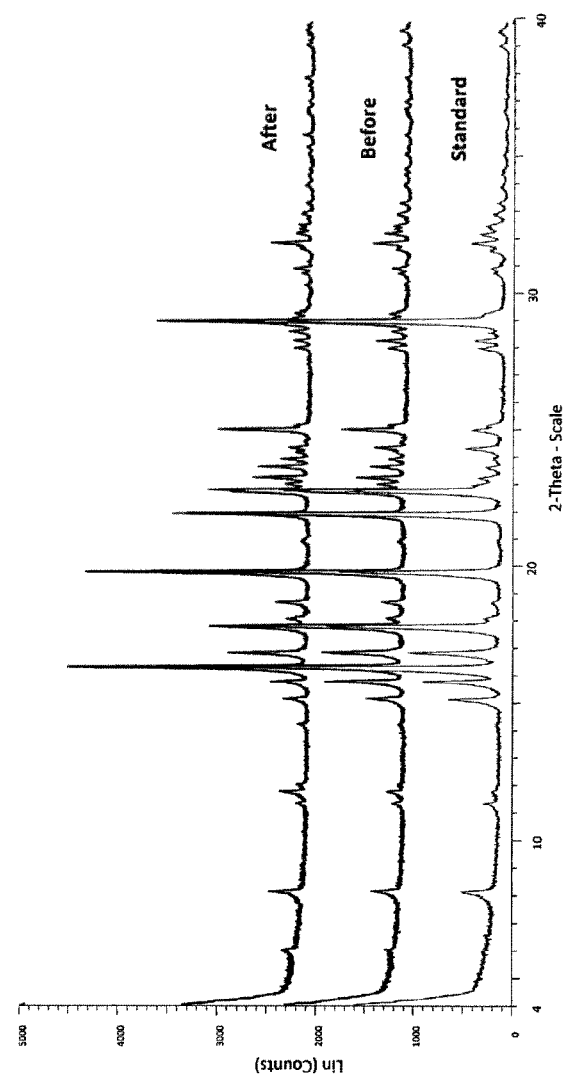
FIG. 6: PXRD pattern of phase I samples before and after grinding. The standard PXRD pattern of phase I is shown for comparison purposes.

In order to verify if the differences in the peak intensities were due to texture effects, some selected samples were gently grinded in an agate mortar and measured. After homogenizing the samples, the texture effects became less pronounced or disappeared (see FIG. 6).

Figure 7:
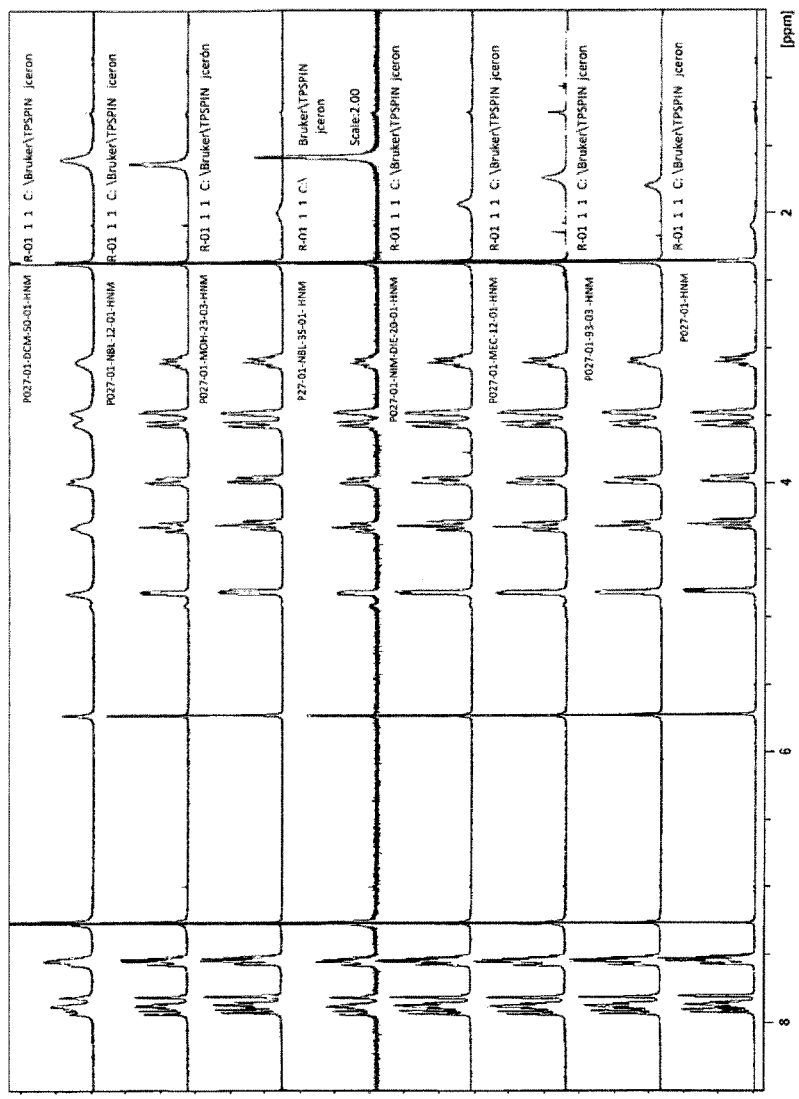
FIG. 7: $^1$H-NMR spectra of the samples depicted in FIG. 6.

In addition, several samples of phase I were analyzed by $^1$H NMR in order to check the stability of the salt. The chemical shifts and the integrations of the $^1$H NMR signals were coincident for all samples and no signs of the lost of HCl or decomposition of the samples could be observed (see FIG. 7).

Figure 3:
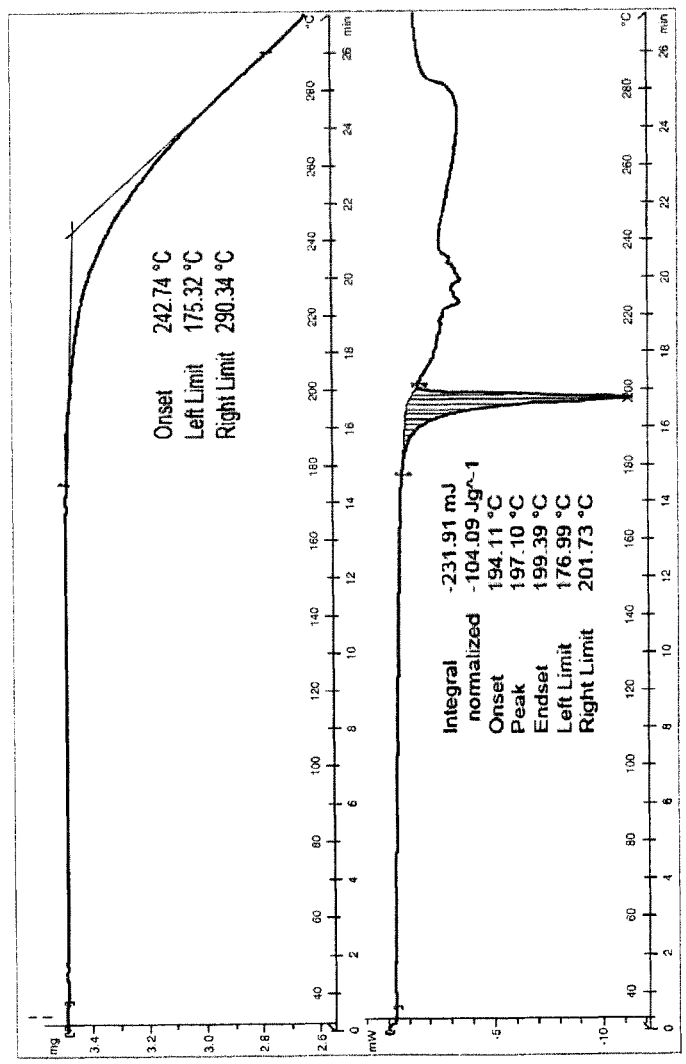
FIG. 3: DSC and TGA analyses of phase I.
Figure 8:
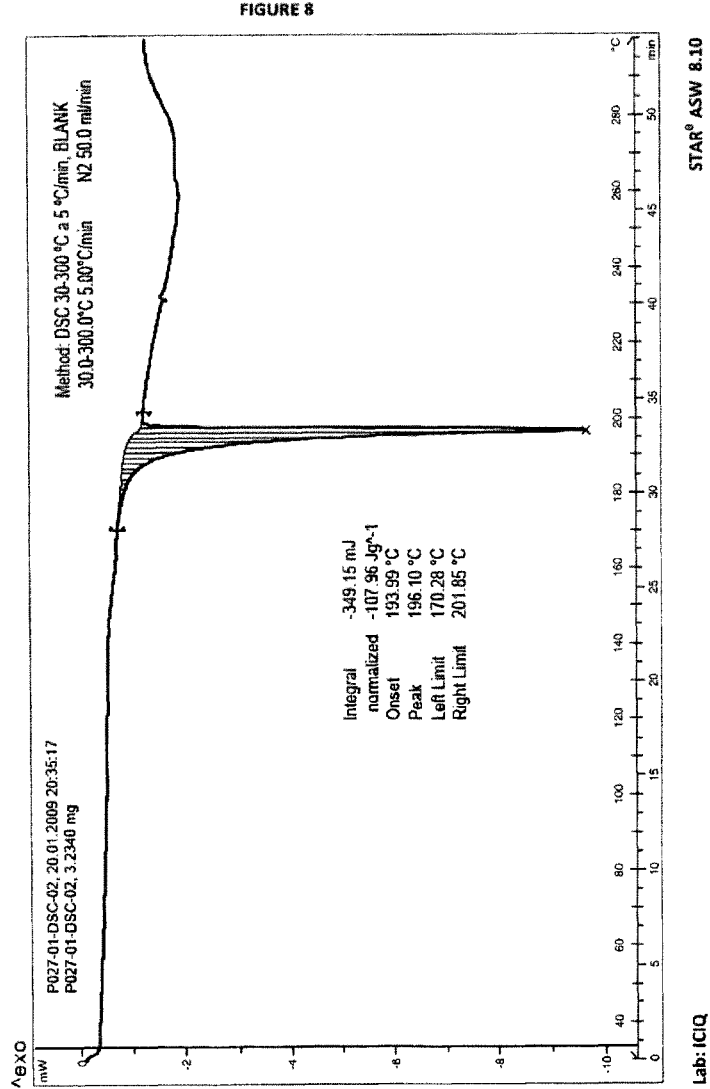
FIG. 8: DSC analysis of phase I at a heating rate of 5° C./min.
Figure 9:
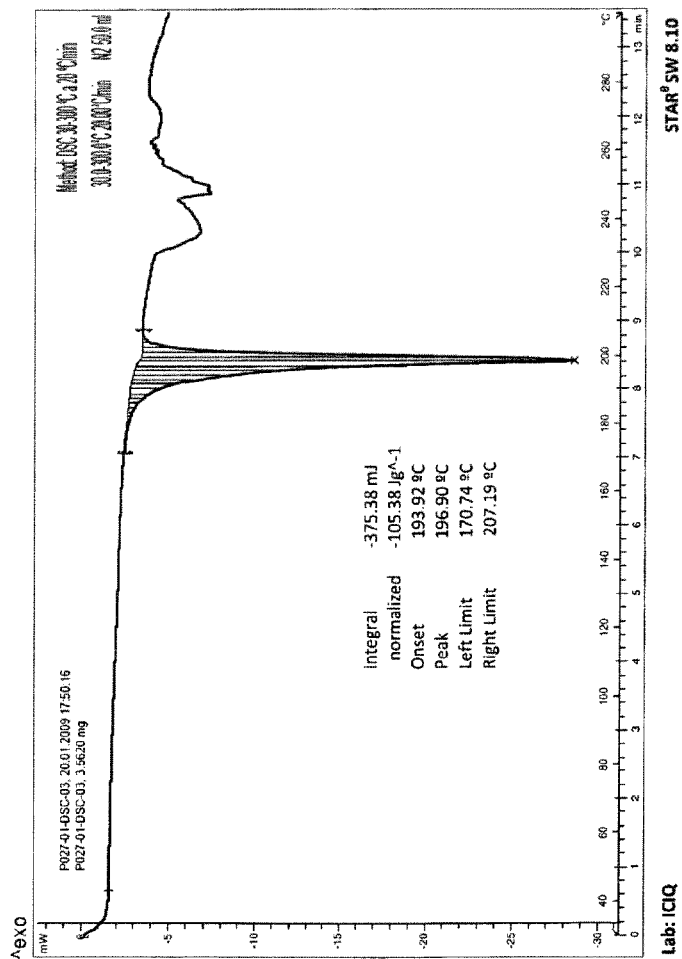
FIG. 9: DSC analysis of phase I at a heating rate of 20° C./min.

A DSC analysis of phase I samples was performed with a heating rate of 10° C./min. The analysis presented a sharp endothermic peak, which does not recover the base line, with an onset at 194° C. and an enthalpy of 103 J/g corresponding to melting followed by decomposition of the product (see FIG. 3). In additional DSC analyses of the same sample, performed with a heating rate of 5° C./min and 20° C./min, it was observed that the onset temperature of the endothermic peak does not vary with the heating rate (see FIGS. 8 and 9).

In a TGA of a phase I sample a weight loss, due to decomposition of the sample, was observed at temperatures higher than 195° C. (see FIG. 3). No weight loss was observed at temperatures below 195° C., indicating the absence of solvent. The onset temperature of weight loss in the TGA coincides with the melting temperature, confirming that the sample decomposes on melting.

Figure 4:
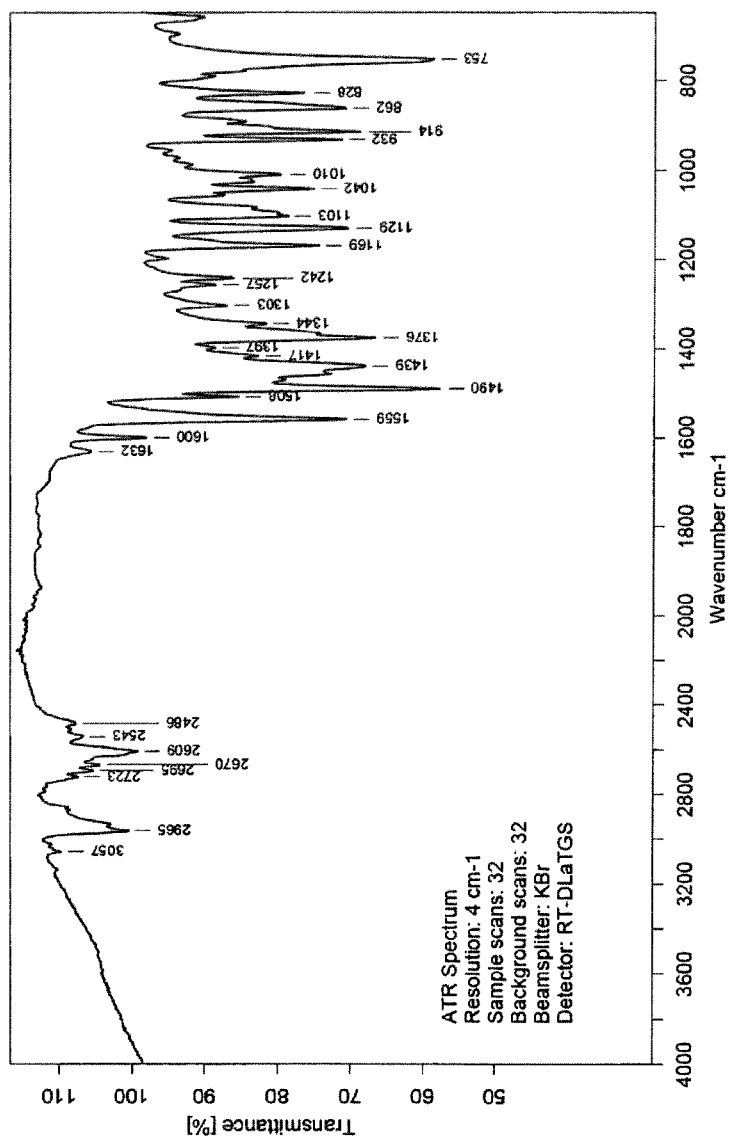
FIG. 4: FTIR analysis of phase I.

The FTIR spectrum of P027 phase I presented intense peaks at about 2965, 2609, 1632, 1600, 1559, 1508, 1490, 1439, 1376, 1301, 1257, 1242, 1169, 1129, 1103, 1042, 1010, 932, 914, 862, 828 and 753 cm$^{-1}$ (see FIG. 4).

Structure determination of 4-[2-[[5-methyl-1-(2-naphthalenyl)-1H-pyrazol-3-yl]oxy]ethyl]morpholine hydrochloride phase I crystalline form by single crystal X-ray diffraction The identity and crystal structure of the P027 compound phase I was assayed by a single crystal X-ray structure determination. Suitable crystals were obtained by slow diffusion of n-heptane into a concentrated solution of the product in acetone. Since the selected crystals were mostly twinned, a small fragment of a plate (0.30×0.30×0.07 mm$^3$) was separated with a micro scalpel and used for single crystal X-ray structure determination. Table 26 shows the measurement conditions utilized, cell constants and results obtained in a single crystal X-ray structure diffraction analysis. Table 27 depicts phase I selected bond distances and angles for an X-ray structure determination performed at 100 K.

TABLE 26

Phase I single crystal X-ray structure diffraction analysis
Measurement conditions, cell constants and results

| Parameter | Value |
| --- | --- |
| Empirical formula | C20 H24 Cl1 N3 O2 |
| Formula weight | 373.87 UMA |
| Temperature | 100(2) K |
| Wavelength | 0.71073 Å |
| Crystal system | Monoclinic |
| Space group | C2/c |
| Unit cell dimensions | a = 29.367(3) Å, α = 90° |
| | b = 11.6704(11) Å, β = 91.284(2)° |
| | c = 11.0437(10) Å, γ = 90° |
| Volume | 3784.0(6) Å$^3$ |
| Z | 8 |
| Density (calculated) | 1.313 Mg/m$^3$ |
| Absorption coefficient | 0.221 mm$^{-1}$ |
| F(000) | 1584 |
| Crystal size | 0.40 × 0.40 × 0.10 mm$^3$ |
| Theta range for data collection | 2.64 to 38.06°. |
| Index ranges | −50 <= h <=50, −20 <= k <= 18, −17 <= l <= 19 |
| Reflections collected | 42960 |
| Independent reflections | 10292 [R(int) = 0.0414] |
| Completeness to theta = 38.06° | 99.5% |
| Absorption correction | SADABS (Bruker-Nonius) |
| Max. and min. transmission | 0.9782 and 0.9167 |
| Refinement method | Full-matrix least-squares on F$^2$ |

TABLE 26-continued

Phase I single crystal X-ray structure diffraction analysis
Measurement conditions, cell constants and results

| Parameter | Value |
| --- | --- |
| Data/restraints/parameters | 10292/0/237 |
| Goodness-of-fit on F2 | 1.043 |
| Final R indices [I > 2sigma(I)] | R1 = 0.0540, wR2 = 0.1409 |
| R indices (all data) | R1 = 0.0733, wR2 = 0.1586 |
| Largest diff. peak and hole | 2.152 and −1.013e.Å$^{-3}$ |

TABLE 27

Phase I bond lengths [Å] and angles [°]

| | |
| --- | --- |
| O(1)—C(1) | 1.3601(12) |
| O(1)—C(15) | 1.4357(13) |
| N(1)—C(3) | 1.3545(14) |
| N(1)—N(2) | 1.3774(12) |
| N(1)—C(4) | 1.4271(13) |
| C(1)—N(2) | 1.3290(13) |
| C(1)—C(2) | 1.4056(14) |
| O(2)—C(18) | 1.4184(15) |
| O(2)—C(19) | 1.4339(16) |
| C(2)—C(3) | 1.3802(14) |
| N(3)—C(16) | 1.4995(13) |
| N(3)—C(20) | 1.5028(13) |
| N(3)—C(17) | 1.5055(13) |
| C(3)—C(14) | 1.4887(15) |
| C(4)—C(5) | 1.3749(14) |
| C(4)—C(13) | 1.4156(15) |
| C(5)—C(6) | 1.4192(14) |
| C(6)—C(7) | 1.4228(15) |
| C(6)—C(11) | 1.4277(14) |
| C(7)—C(8) | 1.3749(16) |
| C(8)—C(9) | 1.4141(18) |
| C(9)—C(10) | 1.3770(16) |
| C(10)—C(11) | 1.4211(14) |
| C(11)—C(12) | 1.4225(14) |
| C(12)—C(13) | 1.3755(14) |
| C(15)—C(16) | 1.5063(14) |
| C(17)—C(18) | 1.5157(15) |
| C(19)—C(20) | 1.5127(15) |
| C(1)—O(1)—C(15) | 114.73(8) |
| C(3)—N(1)—N(2) | 112.83(8) |
| C(3)—N(1)—C(4) | 126.90(9) |
| N(2)—N(1)—C(4) | 120.27(8) |
| N(2)—C(1)—O(1) | 122.26(9) |
| N(2)—C(1)—C(2) | 113.61(8) |
| O(1)—C(1)—C(2) | 124.13(9) |
| C(1)—N(2)—N(1) | 102.71(8) |
| C(18)—O(2)—C(19) | 109.40(9) |
| C(3)—C(2)—C(1) | 104.03(9) |
| C(16)—N(3)—C(20) | 113.52(8) |
| C(16)—N(3)—C(17) | 109.85(8) |
| C(20)—N(3)—C(17) | 108.42(8) |
| N(1)—C(3)—C(2) | 106.81(9) |
| N(1)—C(3)—C(14) | 122.28(9) |
| C(2)—C(3)—C(14) | 130.90(10) |
| C(5)—C(4)—C(13) | 121.24(9) |
| C(5)—C(4)—N(1) | 119.67(9) |
| C(13)—C(4)—N(1) | 119.09(9) |
| C(4)—C(5)—C(6) | 120.37(9) |
| C(5)—C(6)—C(7) | 121.81(9) |
| C(5)—C(6)—C(11) | 118.87(9) |
| C(7)—C(6)—C(11) | 119.32(9) |
| C(8)—C(7)—C(6) | 120.56(11) |
| C(7)—C(8)—C(9) | 120.09(11) |
| C(10)—C(9)—C(8) | 120.77(10) |
| C(9)—C(10)—C(11) | 120.51(10) |
| C(10)—C(11)—C(12) | 122.21(9) |
| C(10)—C(11)—C(6) | 118.74(9) |
| C(12)—C(11)—C(6) | 119.05(9) |
| C(13)—C(12)—C(11) | 121.07(9) |
| C(12)—C(13)—C(4) | 119.39(9) |
| O(1)—C(15)—C(16) | 109.35(8) |
| N(3)—C(16)—C(15) | 113.87(8) |

TABLE 27-continued

| Phase I bond lengths [Å] and angles [°] | |
|---|---|
| N(3)—C(17)—C(18) | 109.94(9) |
| O(2)—C(18)—C(17) | 111.58(9) |
| O(2)—C(19)—C(20) | 111.61(10) |
| N(3)—C(20)—C(19) | 109.54(9) |

Figure 10:
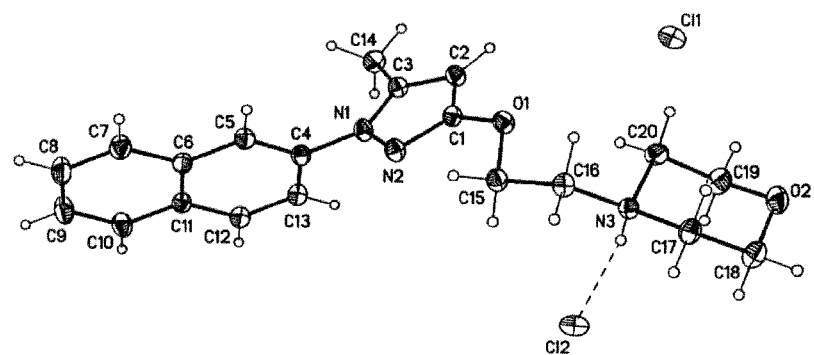
FIG. 10: Ortep-Plot (50%) showing the organic cation and the two independent half chlorine anions contained in the unit cell.
Figure 11:
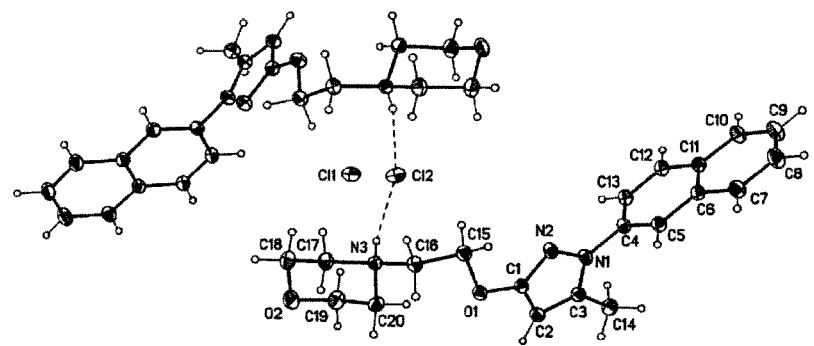
FIG. 11: Ortep-Plot (50%) showing the structure of phase I. The hydrogen bonds are marked with discontinuous lines.

Phase I form crystallizes in the centrosymmetric space C2/c with one cationic molecule and two half independent anionic chlorine atoms in the unit cell (see FIG. 10). Each cationic molecule shares two chlorine anions with neighboring cationic molecules. One of the shared chlorine atoms is linked to the positively charged N—H-groups of two neighboring cationic molecules making two hydrogen bonds (Cl1 . . . N3-distance: 3.13 Å) [see FIGS. 10 and 11]. The second shared chlorine anion is located in the intermolecular space making only weak interactions to the surrounding molecules (shortest distance is Cl2 . . . C17-distance: 3.56 Å).

Figure 12:
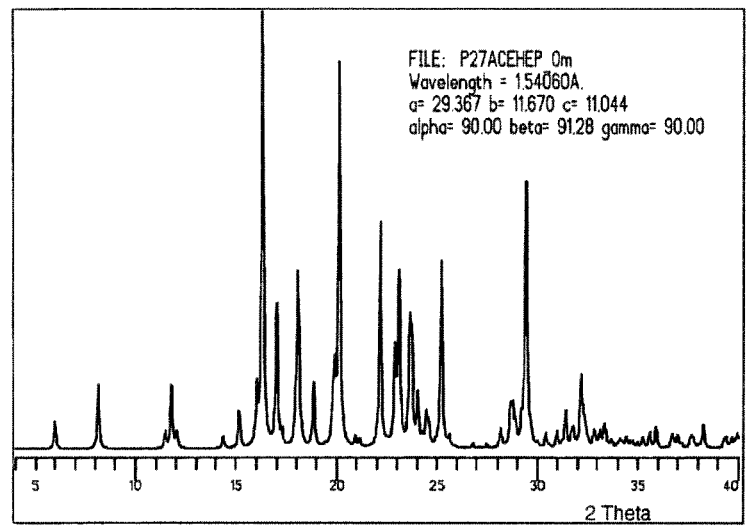
FIG. 12: Simulated powder diffraction pattern generated from the single crystal data of phase I.
Figure 13:
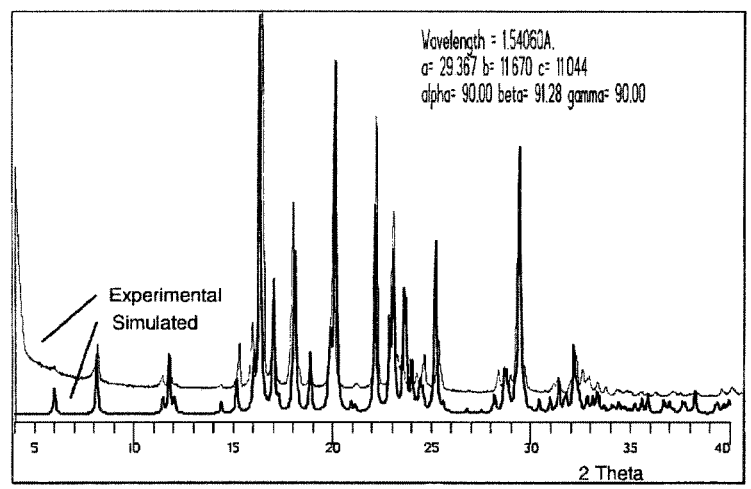
FIG. 13: Comparison of the simulated powder diffraction pattern obtained from single crystal data and the experimentally measured powder diffraction pattern of phase I.

The powder diffraction pattern simulated from the single crystal data shows a good correspondence to the experimentally measured standard powder diffraction pattern of phase I. The overlay confirms the phase purity. Small variations in peak positions are due to the temperature difference at which the compared powder diffractograms were measured (simulated at −173° C. and experimentally measured at room temperature). FIGS. 12 and 13 show the phase I simulated powder diffraction pattern and its comparison to the experimentally measured pattern, respectively.

Example 2

Preparation and characterization of 4-[2-[[5-methyl-1-(2-naphthalenyl)-1H-pyrazol-3-yl]oxy]ethyl]morpholine hydrochloride phase II crystalline form In the initial screening, a mixture of phase I and a phase II was obtained by solvent evaporation in several solvents (methanol, water, diisopropyl ether-water, nitromethane dioxane-water and heptane-water). This new phase II could be reproduced pure in the screening performed using polymers by evaporation of a solution of P027 in water and with the presence of catalytic amounts of poly(vinyl alcohol).

Crystallization of phase II form by solvent evaporation at room temperature: A Sample of 4-[2-[[5-methyl-1-(2-naphthalenyl)-1H-pyrazol-3-yl]oxy]ethyl]morpholine hydrochloride (20-25 mg) was dissolved in the minimum amount of water (0.7 ml) at room temperature and a small quantity of poly(vinyl alcohol) (2-3 mg) was added to the corresponding solution. The resulting solution or suspensions was left to evaporate for two weeks in open vials at room temperature.

Figure 23:
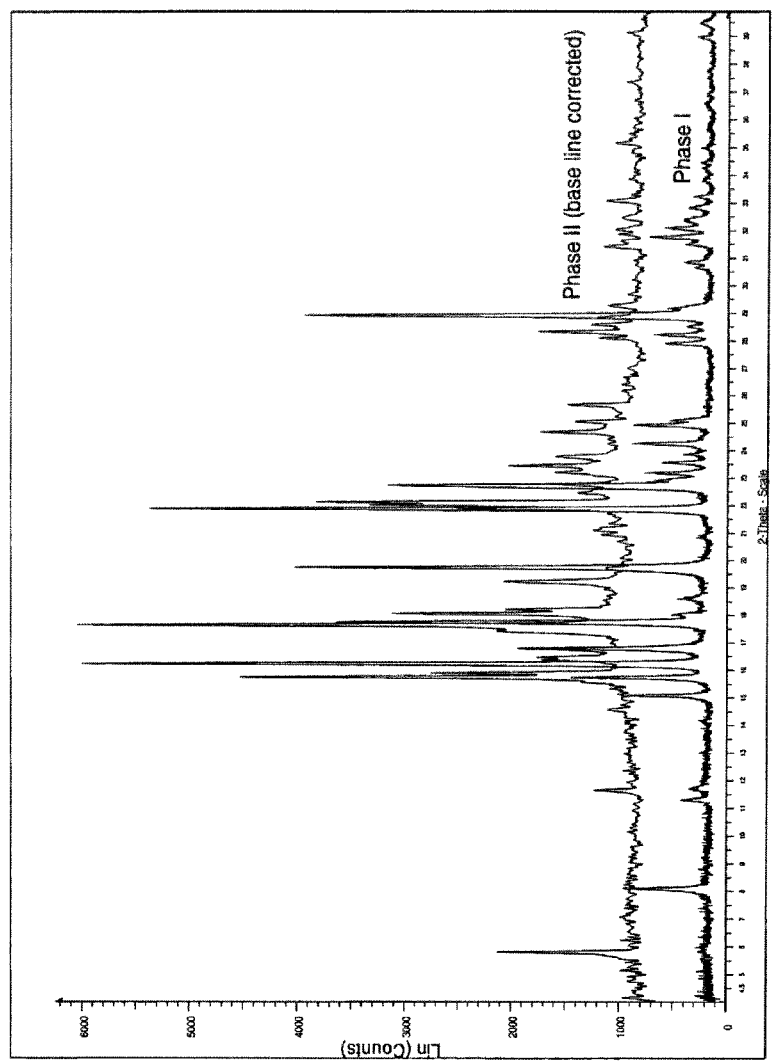
FIG. 23: Comparison of the PXRD patterns obtained for Phase I and Phase II.

A comparison of the PXRD patterns of phase I and phase II is shown in FIG. 23. It can be observed that phase II obtained using poly(vinyl alcohol) is pure and no peaks of phase I can be detected in the pattern.

Figure 24:
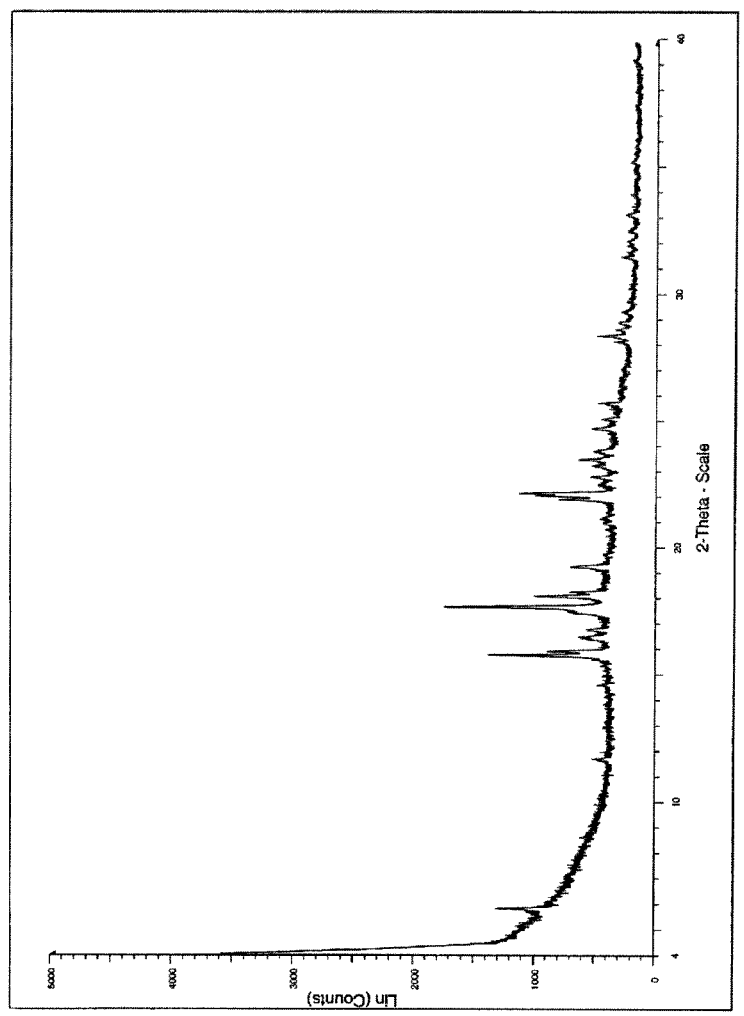
FIG. 24: Standard PXRD pattern of Phase II.

A standard PXRD pattern for phase II form is shown in FIG. 24.

Figure 25:
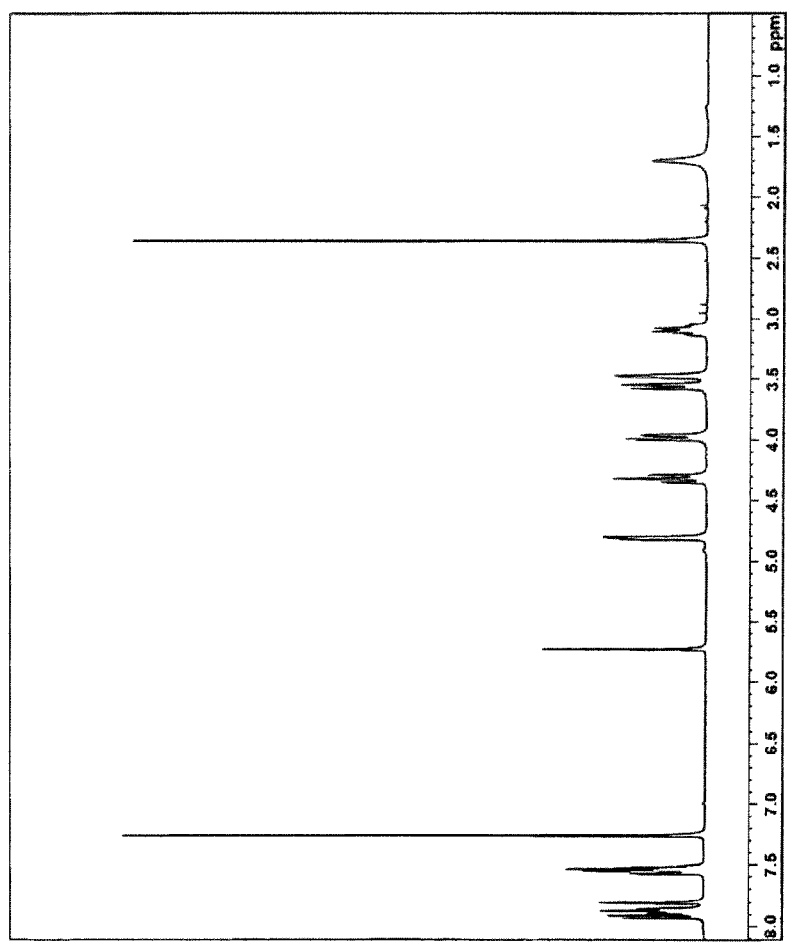
FIG. 25: $^1$H NMR spectrum of Phase II.
Figure 26:
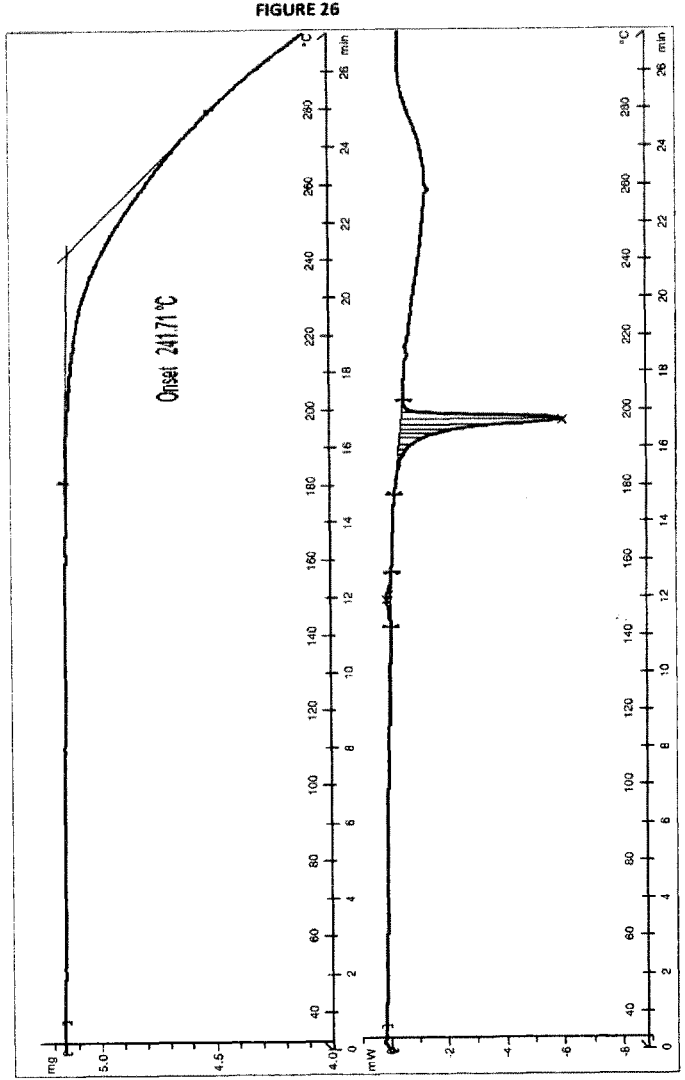
FIG. 26: DSC and TGA analyses of Phase II.

Characterization by $^1$H NMR, DSC and TGA is shown in FIGS. 25 and 26.

The $^1$H NMR spectrum obtained from the mixture of phases I and II is identical to the one obtained for phase I indicating that phase II is not a decomposition product. The spectra obtained for phase I and phase II are compared in FIG. 25. No differences in the shifts of relevant hydrogen atoms can be observed.

The DSC analysis of phase II, performed with a heating rate of 10° C./min, shows a weak broad exothermic peak with an onset at 145° C. and an enthalpy of 4 J/g and a sharp endothermic peak with an onset at 194° C. and an enthalpy of 92 J/g, corresponding to melting followed by decomposition of the product (FIG. 26). The small exothermic peak at 145° C. suggests that phase II should be a metastable phase monotropically related to phase I. Thus, the DSC actually shows a solid-solid transition of phase II to I, followed by fusion of phase I.

In the TG analysis of phase II (FIG. 26) a weight loss, due to decomposition of the sample, is observed at temperatures higher than 195° C. The starting temperature of weight loss in the TGA coincides with the melting temperature, confirming that the sample decomposes on melting. No weight loss is observed at temperatures below 180° C., indicating the absence of solvent. The TG analysis of the solid containing phase II is identical to the one obtained for phase I.

Example 3

Preparation and characterization of 4-[2-[[5-methyl-1-(2-naphthalenyl)-1H-pyrazol-3-yl]oxy]ethyl]morpholine hydrochloride phase III crystalline form Phase III form was generated by polymer induced crystallization. This solid was obtained in four experiments always in the presence of poly(ethylene glycol). In three cases it was obtained by evaporation of water or acetone and in one case it was obtained by addition of diisopropyl ether as antisolvent to a solution in water.

Crystallization of phase form by solvent evaporation at room temperature: A Sample of 4-[2-[[5-methyl-1-(2-naphthalenyl)-1H-pyrazol-3-yl]oxy]ethyl]morpholine hydrochloride (20-25 mg) was dissolved in the minimum amount of water (0.7 ml) or acetone (5.7 ml) at room temperature and a small quantity of poly(ethylene glycol) (2-3 mg) was added to the corresponding solution. The resulting solution or suspensions was left to evaporate for two weeks in open vials at room temperature.

Crystallization of phase form by addition of an antisolvent: A Sample of 4-[2-[[5-methyl-1-(2-naphthalenyl)-1H-pyrazol-3-yl]oxy]ethyl]morpholine hydrochloride (20-25 mg) together with poly(ethylene glycol) (3-4 mg) was dissolved in the minimum amount of water at room temperature and diisopropyl ether (10 ml) was added under vigorous stirring. The final suspension was left evaporate.

Figure 27:
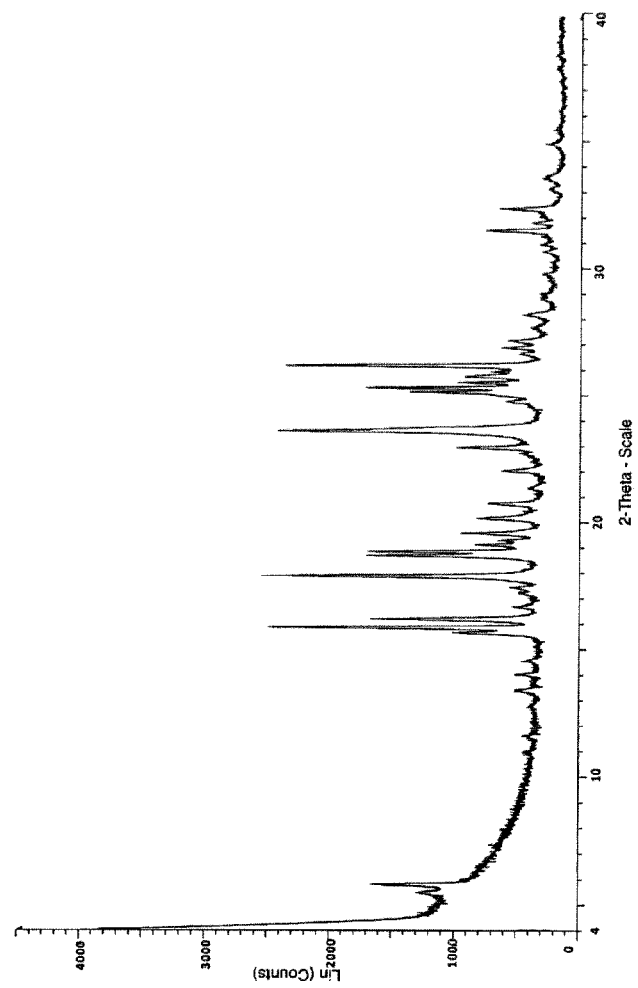
FIG. 27: Standard PXRD pattern of Phase III.
Figure 28:
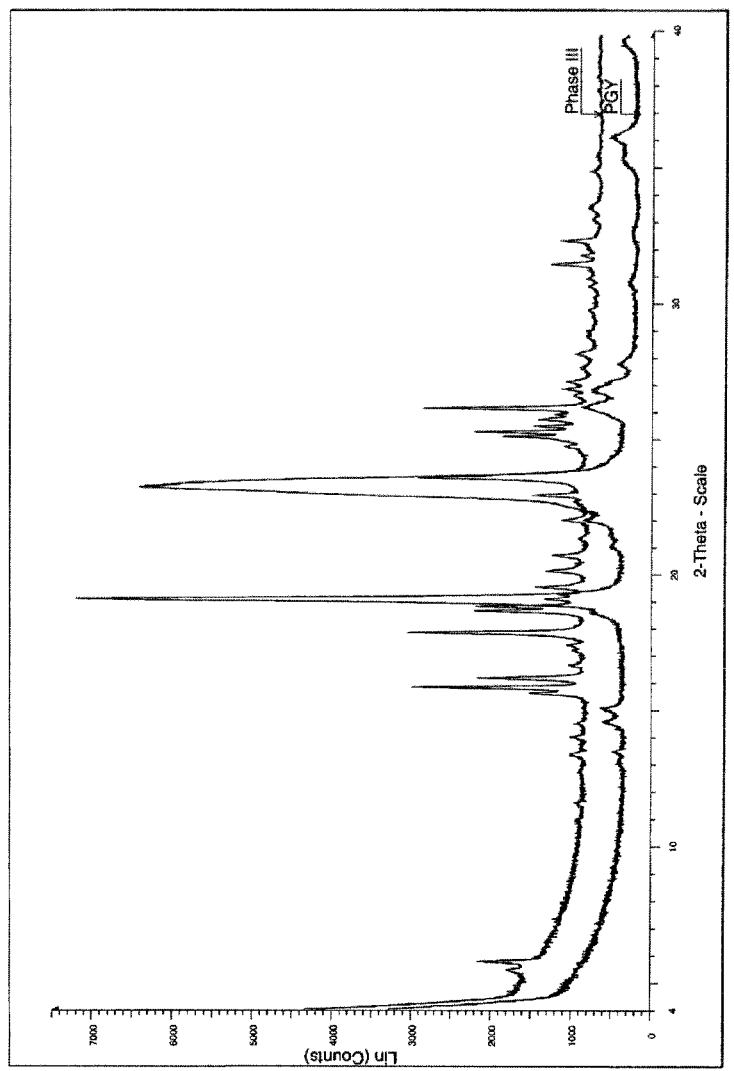
FIG. 28: Comparison of the PXRD patterns obtained for poly(ethylene glycol) and Phase III.

Phase III was characterized by PXRD, $^1$H NMR, DSC and TGA. A representative PXRD pattern for phase III is shown in FIG. 27. By comparing the PXRD pattern of phase III with the pattern of poly(ethylene glycol) the two strongest characteristic signals of the polymer at 19.1° and 23.2° in 2θ can be clearly distinguished (see comparison at FIG. 28). The peak at 19.1° in 2θ can be observed as a weak signal and the broad peak at 23.2° in 2θ can be also observed slightly shifted to 23.6° in 2θ in the pattern of phase III.

Figure 29:
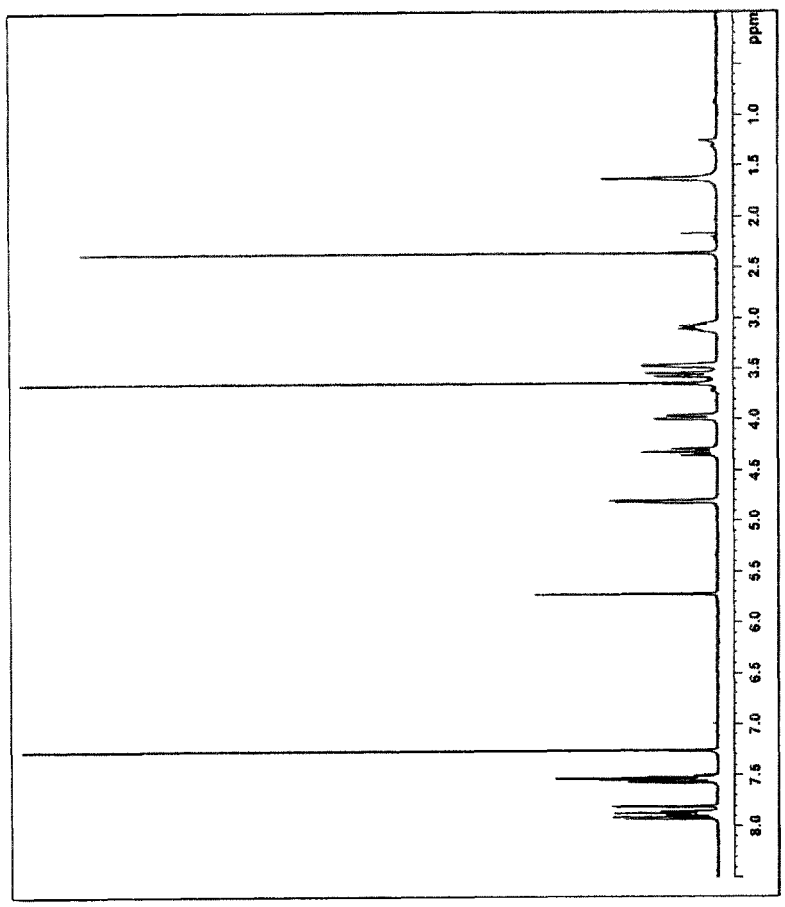
FIG. 29: $^1$H NMR spectrum of Phase III.
Figure 31:
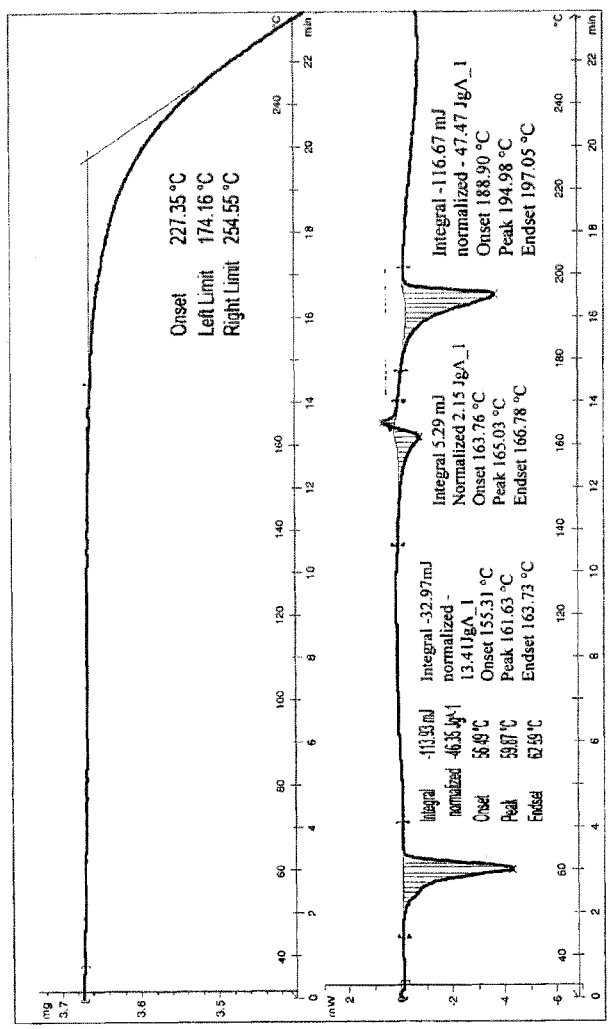
FIG. 31: DSC and TGA analyses of Phase III.

Characterization by $^1$H NMR, DSC and TGA is shown in FIGS. 29 and 31.

Figure 30:
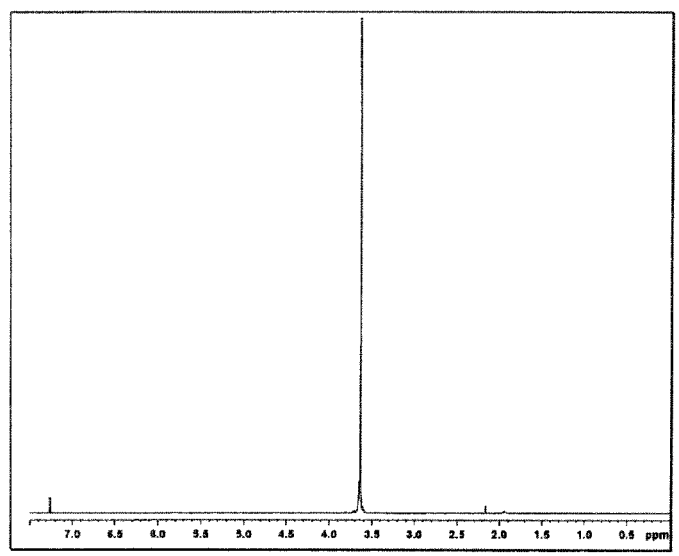
FIG. 30: $^1$H NMR spectrum of poly(ethylene glycol).

In the $^1$H NMR spectrum of phase III the presence of the characteristic signals of P027 indicates that the sample did not decompose. Additionally, in all the spectra measured, the characteristic peak corresponding to poly(ethylene glycol) was observed indicating that phase III is always mixed with this polymer. The $^1$H NMR spectrum of poly(ethylene glycol) is represented in FIG. 30.

Figure 32:
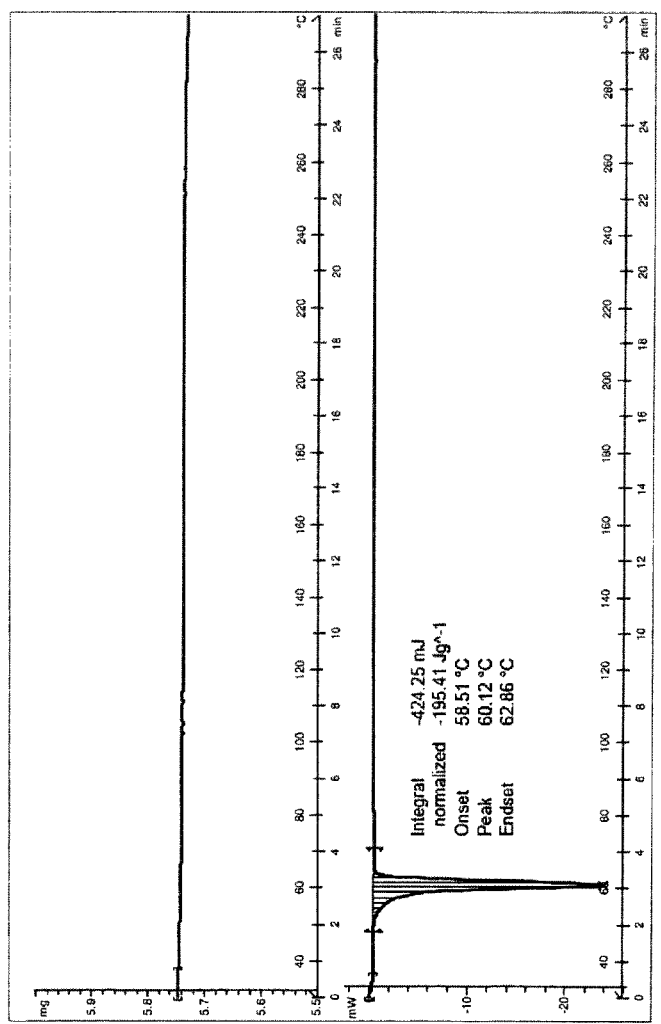
FIG. 32: DSC and TGA analyses of poly(ethylene glycol).
Figure 33:
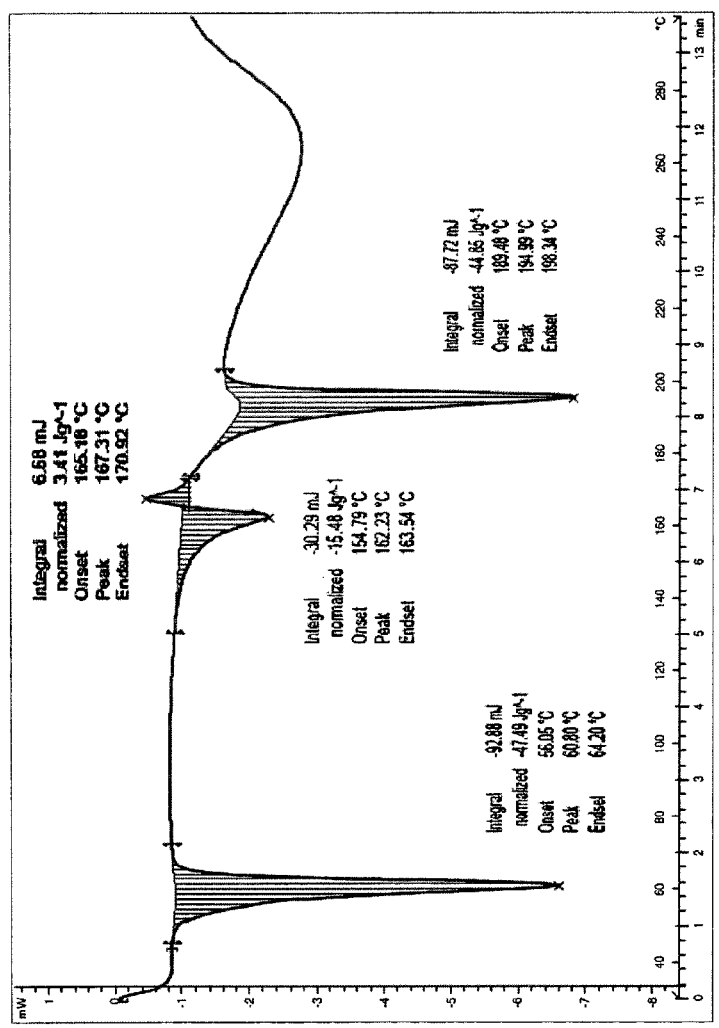
FIG. 33: DSC analyses of Phase III with a heating rate of 20° C./min.
Figure 34:
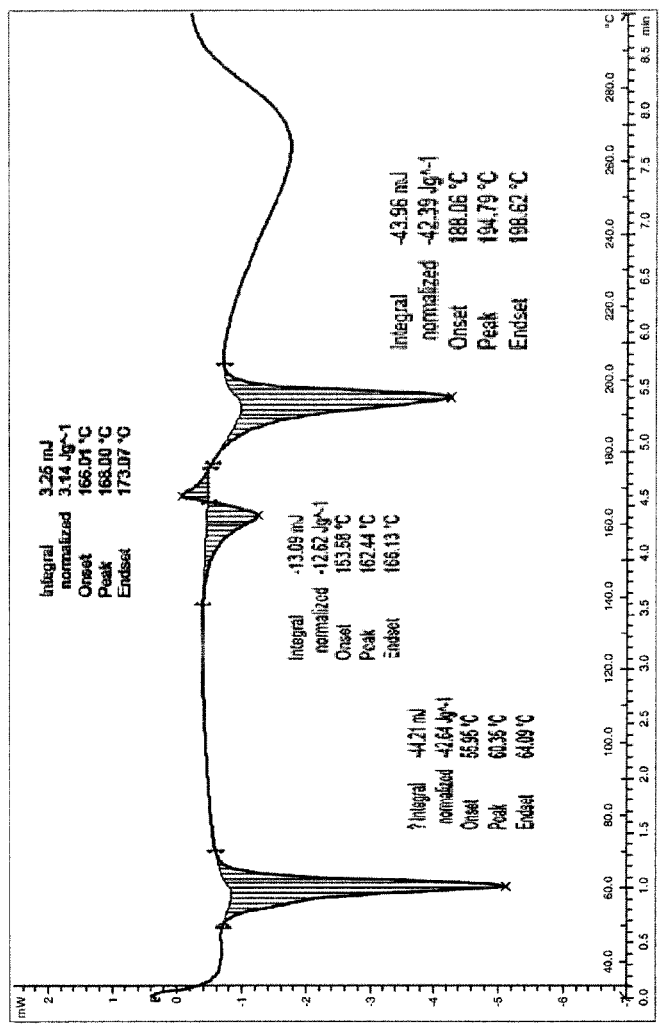
FIG. 34: DSC analyses of Phase III with a heating rate of 30° C./min.

The DSC analysis of Phase III (see FIG. 31), performed with a heating rate of 10° C./min, presents a first sharp endothermic peak with an onset at 56° C. and an enthalpy of 46 J/g corresponding to melting of poly(ethylene glycol). The DSC of pure poly(ethylene glycol) is shown in FIG. 32. In the range from 150 to 170° C. the DSC shows a double peak, first endothermic and then exothermic, corresponding probably to melting of phase III overlapped with recrystallization to phase I. Finally, an endothermic peak with an onset at 190° C. and an enthalpy of 47 J/g, corresponding to melting followed by decomposition of phase I can be observed. Additionally, DSC analyses of the same sample, performed with a heating rate of 20° C./min (FIG. 33) and 30° C./min (FIG. 34) were performed showing that the onset temperature of the endothermic peaks do not vary with the heating rate. This indicates that the endothermic peaks correspond to melting points.

In the TG analysis of Phase III (FIG. 31) a weight loss, due to decomposition of the sample, is observed at temperatures higher than 180° C. No weight loss is observed at temperatures below 180° C., indicating the absence of solvent. The onset temperature of weight loss in the TGA coincides with the melting temperature, confirming that the sample decomposes on melting.

Example 4

Preparation and characterization of 4-[2-[[5-methyl-1-(2-naphthalenyl)-1H-pyrazol-3-yl]oxy]ethyl]morpholine hydrochloride phase IV crystalline form Phase IV form was only generated by polymer induced crystallization. This phase was formed in experiments performed using chloroform as solvent and diisopropyl ether as antisolvent. Phase IV solid was obtained with the following polymers: polyvinyl pyrrolidone (PVP), poly(acrylic acid) (PAA), polypropylene (PPL), poly(styrene-co-divinylbenzene) (PSV), poly(tetrafluoroethylene) (PTF), poly(vinyl alcohol) (PVH), polyacrylamide (PAD) and poly(methyl methacrilate) (PMM). Polymers PVP, PAA, PSV, PVH, PAD and PMM are amorphous and polymers PPL and PTF are crystalline. Only in the sample of phase IV obtained with crystalline PTF, a weak peak of the polymer could be detected in the PXRD pattern.

Crystallization of phase form by addition of an antisolvent: A Sample of 4-[2-[[5-methyl-1-(2-naphthalenyl)-1H-pyrazol-3-yl]oxy]ethyl]morpholine hydrochloride (20-25 mg) together with 3-4 mg of the corresponding polymer (polyvinyl pyrrolidone, poly(acrylic acid, polypropylene, poly(styrene-co-divinylbenzene, poly(tetrafluoroethylene), poly(vinyl alcohol), polyacrylamide, poly(methyl methacrilate)), was dissolved in the minimum amount of chloroform at room temperature and diisopropyl ether (2 ml) was added under vigorous stirring. The final solid obtained was separated by centrifugation.

Phase IV form was characterized by PXRD, NMR, DSC and TGA.

Figure 35:
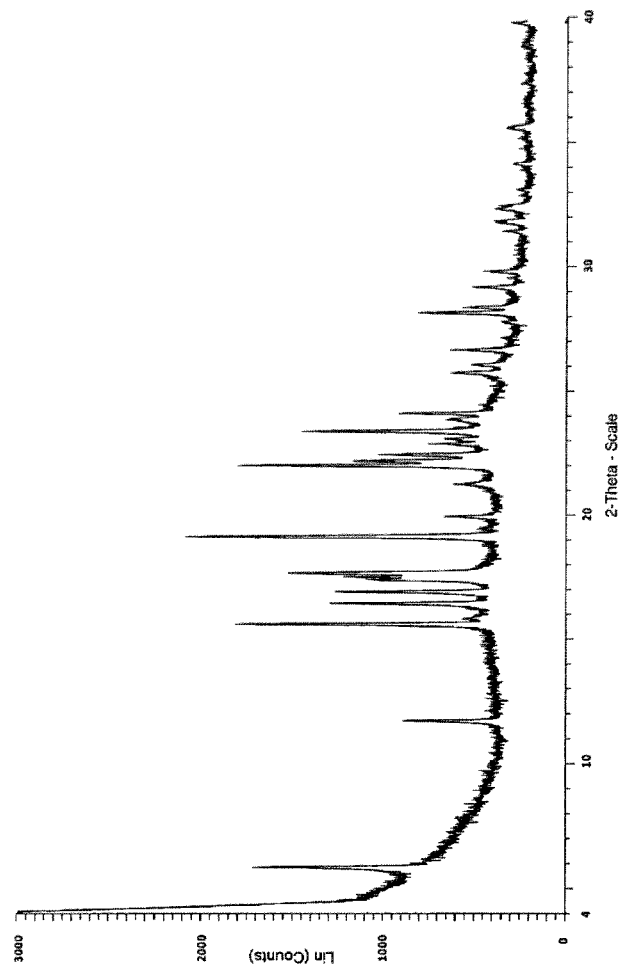
FIG. 35: Standard PXRD pattern of Phase IV.

A representative PXRD pattern for Phase IV is shown in FIG. 35.

Figure 36:
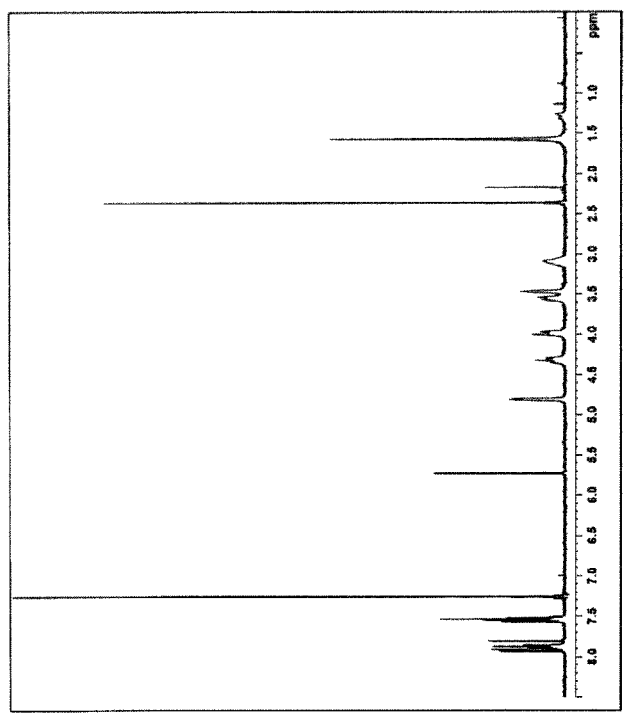
FIG. 36: $^1$H NMR spectrum of Phase IV.
Figure 37:
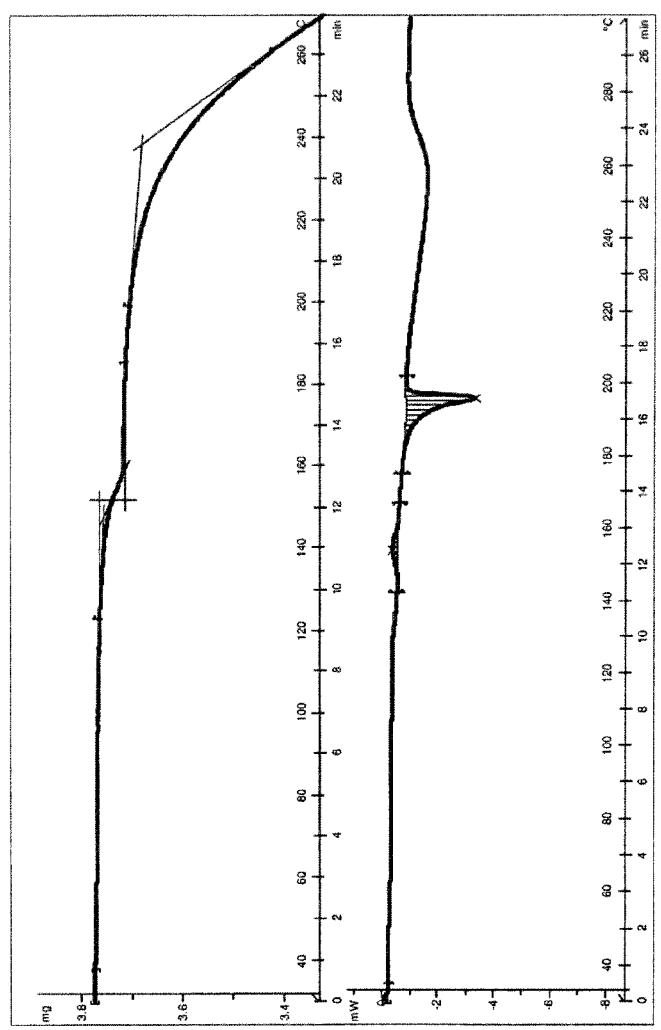
FIG. 37: DSC and TGA analyses of Phase IV.

Characterization by $^1$H NMR, DSC and TGA is shown in FIGS. 36 and 37.

In the $^1$H NMR spectrum of phase IV (see FIG. 36) the presence of the characteristic signals of P027 indicates that the sample did not decompose. No signals corresponding to the polymers could be detected.

The DSC analysis of Phase IV (see FIG. 37), performed with a heating rate of 10° C./min, presents a broad exothermic peak with an onset at 147° C. and an enthalpy of 9 J/g corresponding probably to the solid-solid transition of phase IV to phase I. Finally, an endothermic peak with an onset at 191° C. and an enthalpy of 71 J/g, corresponding to melting followed by decomposition of Phase I can be observed.

In the TG analysis of Phase IV (FIG. 37) a small weight loss, corresponding to a 1.4% of the sample, can be observed between 120 and 170° C. Decomposition of the sample is observed at temperatures higher than 190° C. The weight loss probably corresponds to small quantities of water or dichloromethane which is lost in the transition process. The onset temperature of the higher weight loss in the TGA coincides with the melting temperature, confirming that the sample decomposes on melting.

Example 5

Figure 38:
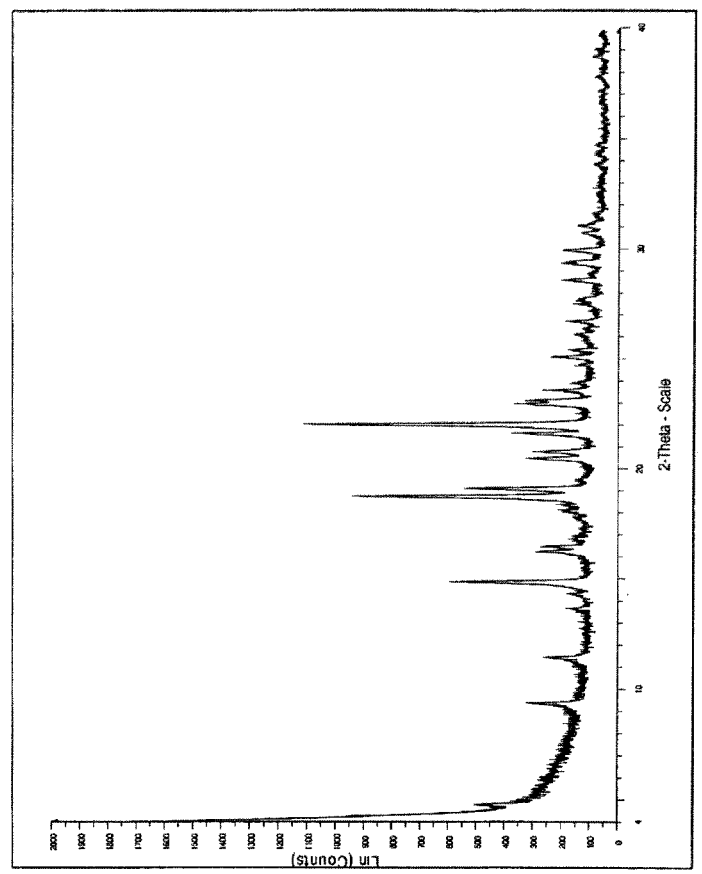
FIG. 38: Standard PXRD pattern of the dioxane solvate.
Figure 39:
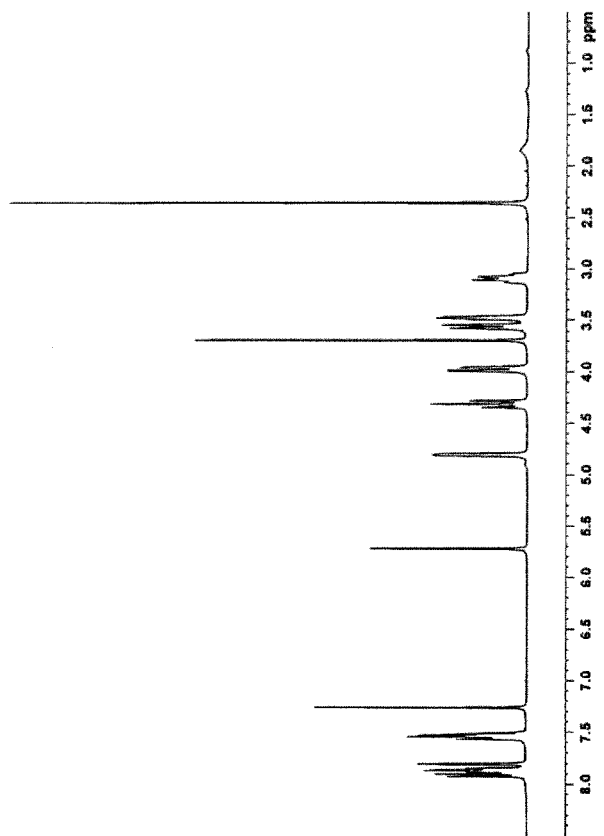
FIG. 39: NMR spectrum of the dioxane solvate.

Preparation and characterization of 4-[2-[[5-methyl-1-(2-naphthalenyl)-1H-pyrazol-3-yl]oxy]ethyl]morpholine hydrochloride solvate with dioxane A new crystalline solvated phase, labeled dioxane solvate, was obtained in a solvent drop grinding experiment in dioxane and by crystallization from a hot saturated solution in dioxane. The dioxane solvate crystallizes in form of small sticky crystallites. A representative PXRD pattern of the solvate is shown in FIG. 38. Characterization by $^1$H NMR, DSC, TGA and FTIR is shown in FIGS. 39 to 41.

Grinding experiment: 50 mg of compound together with catalytic quantities of dioxane (three drops) were grinded in a ball mill at 30 s$^{-1}$ for 30 minutes. For the grinding experiments a Retsch MM400 Ball Mill was used.

Crystallization from a hot saturated solution: 0.5 g of 4-[2-[[5-methyl-1-(2-naphthalenyl)-1H-pyrazol-3-yl]oxy]ethyl] morpholine hydrochloride was dissolved in dioxane (80 mL) at 80° C. The resulting solution was cooled to 40° C. and a solid started to crystallize. The resulting suspension was kept at 40° C. for 2 hours under gentle stirring, cooled to room temperature and kept at that temperature for 2 hours under gentle stirring. The final solid was filtered off.

Figure 40:
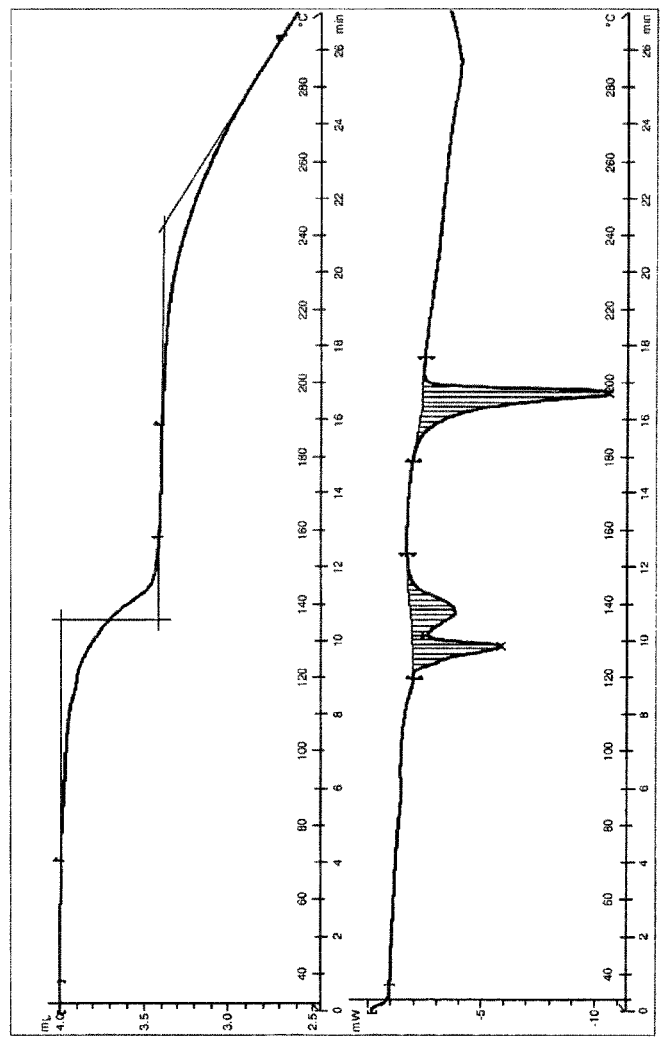
FIG. 40: DSC and TGA analyses of the dioxane solvate.
Figure 41:
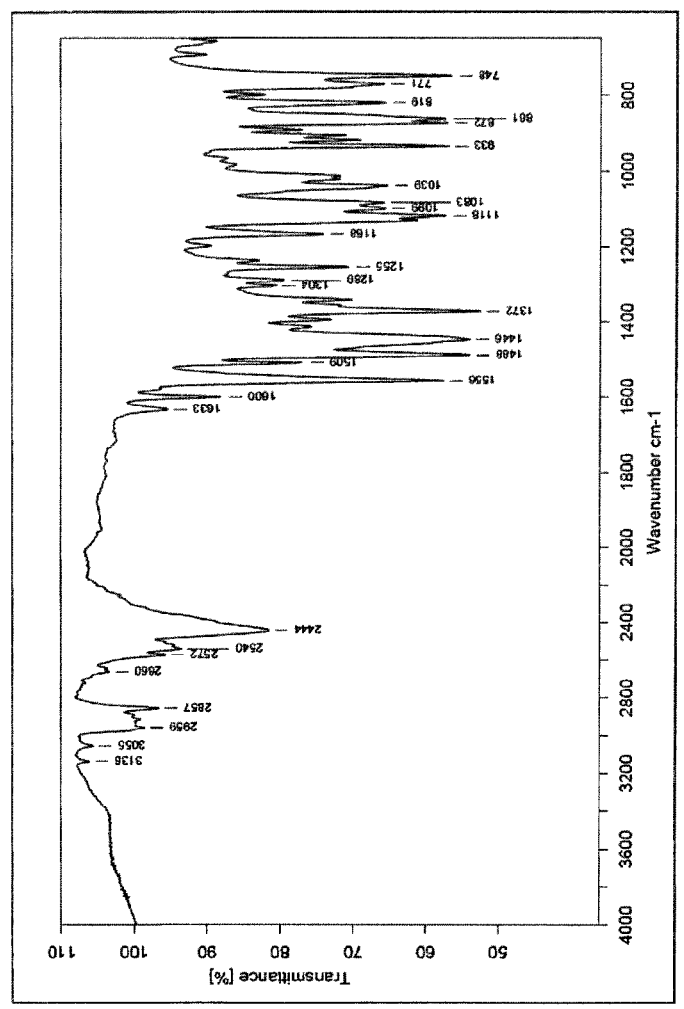
FIG. 41: FTIR analysis of the dioxane solvate.

The DSC analysis of the dioxane solvate, with a heating rate of 10° C./min, presents two overlapped endothermic peaks with onsets at 124° C. and 130° C., probably due to the loss of dioxane, and a third sharp endothermic peak with an onset at 192° C. and an enthalpy of 73 J/g, corresponding to melting followed by decomposition of the product (FIG. 40).

In the TG analysis of the dioxane solvate (FIG. 40) a weight loss of 14.6%, due to the loss of dioxane (theoretical dioxane content for a dioxane monosolvate is 19%), can be observed between 100 and 160° C. Decomposition of the sample is observed at temperatures higher than 190° C. The onset temperature of weight loss due to decomposition in the TGA coincides with the endothermic peak at the DSC, confirming that the sample decomposes on melting. In the $^1$H NMR spectrum the characteristic signal of dioxane can be observed confirming the presence of this solvent (see FIG. 39).

The FTIR spectrum characteristic for the dioxane solvate is represented in FIG. 41 and presents intense peaks at 3138, 3055, 2959, 2857, 2660, 2572, 2540, 2444, 1633, 1600, 1556, 1509, 1488, 1446, 1372, 1304, 1289, 1255, 1168, 1118, 1099, 1083, 1039, 933, 872, 861, 819, 771 and 748 cm$^{-1}$.

The scale-up of the dioxane solvate was performed starting from 50, 100 and 500 mg of the compound. The results obtained in each case are gathered in table 28.

TABLE 28

Scale-up of dioxane solvate

| Entry | Scale[1] | N° exp. | Procedure | Solvent | Observations |
|---|---|---|---|---|---|
| 1 | 50 mg | 3 | grinding | dioxane | solvate |
| 2 | 100 mg | 1 | crystallization from hot saturated solution | dioxane | solvate |
| 3 | 500 mg | 3 | crystallization from hot saturated solution | dioxane | solvate |

[1]Referred to starting compound P027

The solids obtained in the initial screening and in the scale-up at 100 and 500 mg gave the same crystalline phase. At 50 mg scale, the solid was obtained by solvent drop grinding experiments in dioxane. At 100 mg and 500 mg scale, the solid crystallized during cooling to room temperature a hot saturated solution in dioxane.

Example 6

Figure 42:
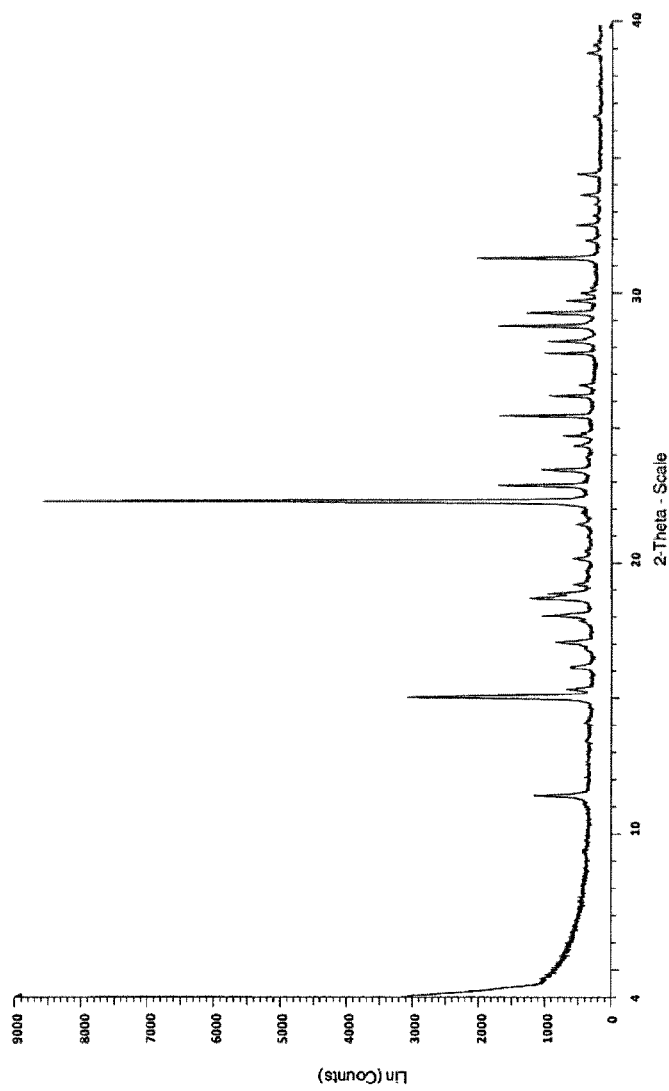
FIG. 42: Standard PXRD pattern of the chloroform solvate.

Preparation and characterization of 4-[2-[[5-methyl-1-(2-naphthalenyl)-1H-pyrazol-3-yl]oxy]ethyl]morpholine hydrochloride solvate with chloroform A new crystalline solvated phase, labeled chloroform solvate, was obtained in polymer induced crystallizations. The chloroform solvate of P027 was obtained by evaporation of a chloroform solution or by crystallization of hot saturated chloroform solutions using the following polymers: poly(ethylene glycol) (PGY), polyvinyl pyrrolidone (PVP), poly(acrylic acid) (PAA), nylon 6/6 (NYL), polypropylene (PPL), poly(tetrafluoroethylene) (PTF), poly(vinyl acetate) (PVA), poly(vinyl alcohol) (PVH), polyacrylamide (PAD) and polysulfone (PLS). The polymers PGY, PPL and PTF are crystalline and the rest amorphous. No signals of the crystalline polymers could be observed in the PXRD patterns. The chloroform solvate crystallizes in the majority of the cases in form of large crystals which are probably stabilized by the presence of the polymers. A representative PXRD pattern of the solvate is shown in FIG. 42. Characterization by DSC and TGA is shown in FIG. 43.

Crystallization of chloroform solvate by solvent evaporation: A Sample of 4-[2-[[5-methyl-1-(2-naphthalenyl)-1H-pyrazol-3-yl]oxy]ethyl]morpholine hydrochloride (20-25 mg) was dissolved in 0.6 mL of chloroform and 3-4 mg of the corresponding polymer (poly(ethylene glycol), polyvinyl pyrrolidone, poly(acrylic acid), nylon 6/6, polypropylene, poly(tetrafluoroethylene), poly(vinyl acetate), poly(vinyl alcohol), polyacrylamide, polysulfone) was added. The suspension was left to evaporate. After 24 hours, the solid obtained was analyzed by PXRD, DSC and TGA.

Figure 43:
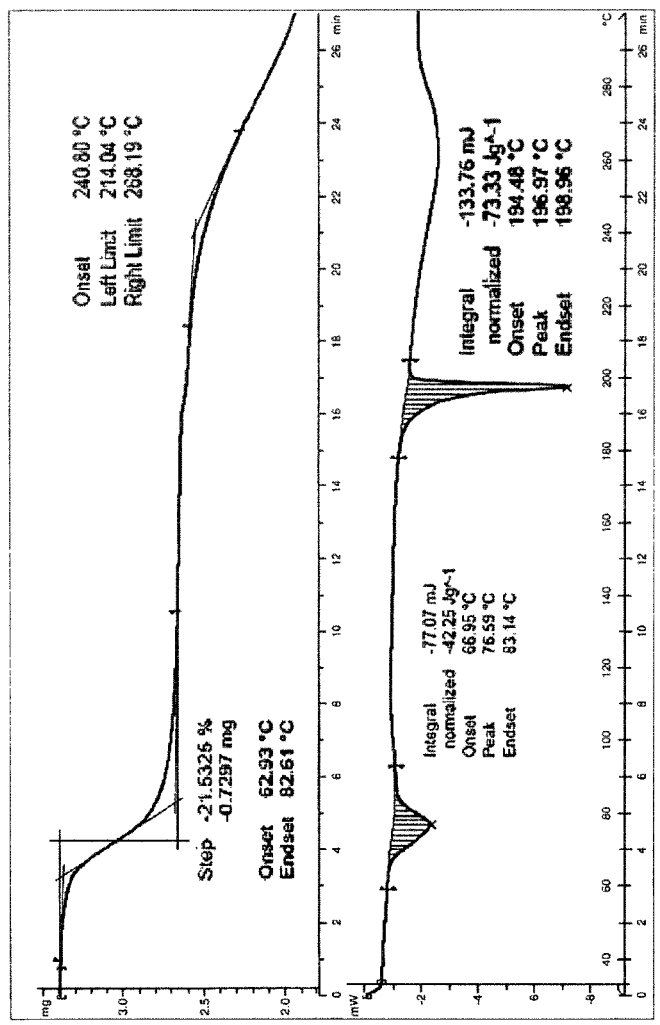
FIG. 43: DSC and TGA analyses of the chloroform solvate.

The DSC analysis of the chloroform solvate measured with a heating rate of 10° C./min, presents a broad endothermic peak with an onset at 67° C. and an enthalpy of 42 J/g, due to the loss of chloroform, and a second sharp endothermic peak with an onset at 194° C. and an enthalpy of 73 J/g, corresponding to melting followed by decomposition of phase I (FIG. 43).

In the TG analysis of the chloroform solvate (FIG. 43) a weight loss of 21.5%, due to the No of chloroform (theoretical chloroform content for a chloroform monosolvate is 22.6%) can be observed between 50 and 120° C. Decomposition of the sample is observed at temperatures higher than 190° C.

The invention claimed is:
1. A solid polymorphic or solvated form of the hydrochloride salt of 4-[2-[[5-methyl-1-(2-naphthalenyl)-1H-pyrazol-3-yl]oxy]ethyl]morpholine selected from the group consisting of:
   a) a polymorphic phase I form having a X-ray powder diffraction pattern showing characteristic peaks at a reflection angle [2θ in degrees] of about 5.9, 8.1, 11.3, 11.7, 14.2, 15.1, 15.8, 16.3, 16.8, 17.8, 18.1, 18.6, 19.8, 20.9, 21.9, 22.8, 23.0, 23.2, 23.6, 23.9, 24.3, 25.0, 25.1, 28.0, 28.3, 28.6, 29.0, 29.2, 30.7, and 30.9;
   b) a polymorphic phase II form having a X-ray powder diffraction pattern showing characteristic peaks at a reflection angle [2θ in degrees] of about 5.776, 11.629, 14.558, 15.737, 15.891, 16.420, 16.740, 17.441, 17.635, 18.056, 18.219, 19.232, 19.712, 20.140, 20.685, 21.135, 21.889, 22.108, 22.478, 22.763, 23.219, 23.454, 23.782, 24.689, 25.065, and 25.671;
   c) a polymorphic phase III form having a X-ray powder diffraction pattern showing characteristic peaks at a reflection angle [2θ in degrees] of about 5.437, 5.714, 10.918, 11.546, 12.704, 13.344, 13.984, 14.505, 15.606, 15.824, 16.164, 16.646, 17.333, 17.837, 18.719, 18.878, 19.236, 19.533, 20.142, 20.689, 21.337, 22.008, 22.929, 23.596, 24.748, 25.064, 25.207, 25.737, and 26.148;
   d) a polymorphic phase IV form, preferably having a X-ray powder diffraction pattern showing characteristic peaks at a reflection angle [2θ in degrees] of about 5.805, 11.685, 15.559, 15.804, 16.397, 16.879, 17.357, 17.465, 17.621, 19.112, 19.435, 19.923, 21.224, 21.987, 22.167, 22.412, 2.852, 23.059, 23.359, 23.855, 24.092, 25.722, 26.054, 26.649, and 27.780;
   e) a dioxane solvate having a X-ray powder diffraction pattern showing characteristic peaks at a reflection angle [2θ in degrees] of about 4.734, 9.317, 11.390, 13.614, 14.290, 14.815, 16.211, 16.432, 16.782, 17.741, 18.056, 18.329, 18.724, 19.070, 19.494, 20.436, 20.762, 21.587, 22.000, 22.935, 23.084, 23.551, 23.891, 24.721, and 25.078; and
   f) a chloroform solvate having a X-ray powder diffraction pattern showing characteristic peaks at a reflection angle [2θ in degrees] of about 11.370, 13.396, 14.048, 15.010, 15.303, 16.117, 16.804, 17.040, 17.830, 18.029, 18.661, 18.859, 19.190, 20.150, 20.434, 21.424, 22.279, 22.871, 23.449, 23.918, 24.343, 24.709, 24.820, 25.459, and 26.199;
with the 2θ values being obtained using copper radiation ($Cu_{K\alpha1}$ 1.54060 Å).

2. A process for the preparation of the polymorphic phase I form as defined in claim 1, comprising;
   a) dissolving 4-[2-[[5-methyl-1-(2-naphthalenyl)-1H-pyrazol-3-yl]oxy]ethyl]morpholine hydrochloride in a suitable solvent, and
   b) evaporating the solvent.

3. The process according to claim 2, wherein 4-[2-[[5-methyl-1-(2-naphthalenyl)-1H-pyrazol-3-yl]oxy]ethyl]morpholine hydrochloride is dissolved at a temperature ranging from room temperature to 120° C. and/or the solvent is evaporated at a temperature ranging from −21° C. to 60° C.

4. A process for the preparation of the polymorphic phase I form as defined in claim 1, comprising mixing a solution comprising 4-[2-[[5-methyl-1-(2-naphthalenyl)-1H-pyrazol-3-yl]oxy]ethyl]morpholine hydrochloride with a suitable antisolvent.

5. The process according to claim 4, wherein the mixing is performed at a temperature ranging from room temperature to 90° C.

6. The process according to claim 4, wherein the mixing is performed by a liquid-liquid diffusion or a gas-liquid diffusion.

7. The process according to claim 2, further comprising adding water to the solution.

8. A process for the preparation of the polymorphic phase I form as defined in claim 1, comprising preparing a suspension comprising 4-[2-[[5-methyl-1-(2-naphthalenyl)-1H-pyrazol-3-yl]oxy]ethyl]morpholine hydrochloride.

9. The process according to claim 8, wherein the suspension is maintained at a temperature ranging from room temperature to 80° C.

10. A process for the preparation of the polymorphic phase II form as defined in claim 1, comprising:
   a) dissolving the hydrochloride salt of 4-[2-[[5-methyl-1-(2-naphthalenyl)-1H-pyrazol-3-yl]oxy]ethyl]morpholine in water in the presence of catalytic amounts of poly(vinyl alcohol), and
   b) evaporating the water.

11. A process for the preparation of the polymorphic phase III form as defined in claim 1, comprising:
   a) dissolving the hydrochloride salt of 4-[(2-[[5-methyl-1-(2-naphthalenyl)-1H-pyrazol-3-yl]oxy]ethyl]morpholine in water or acetone in the presence of catalytic amounts of poly(ethylene glycol), and
   b) evaporating the water or the acetone;
or comprising:
   a) dissolving the hydrochloride salt of 4-[2-[[5-methyl-1-(2-naphthalenyl)-1H-pyrazol-3-yl]oxy]ethyl]morpholine in water in the presence of catalytic amounts of poly(ethylene glycol), and
   b) adding diisopropyl ether as antisolvent.

12. A process for the preparation of the polymorphic phase IV form as defined in claim 1, comprising:
   a) dissolving the hydrochloride salt of 4-[2-[[5-methyl-1-(2-naphthalenyl)-1H-pyrazol-3-yl]oxy]ethyl]morpholine in chloroform in the presence of catalytic amounts of a polymer selected from the group consisting of: polyvinyl pyrrolidone, poly(acrylic acid), polypropylene, poly(styrene-co-divinylbenzene), poly(tetrafluoroethylene), poly(vinyl alcohol), polyacrylamide and poly(methyl methacrilate), and
   b) adding diisopropyl ether as antisolvent.

13. A process for the preparation of the dioxane solvate as defined in claim 1, comprising:
   a) solvent drop grinding comprising:
      a) charging the hydrochloride salt of 4-[2-[[5-methyl-1-(2-naphthalenyl)-1H-pyrazol-3-yl]oxy]ethyl]morpholine together with catalytic quantities of dioxane to a ball mill container; and
      b) grinding; or
   b) crystallization from a hot saturated solution of dioxane.

14. A process for the preparation of the chloroform solvate as defined in claim 1, comprising:
   a) dissolving the hydrochloride salt of 4-[2-[[5-methyl-1-(2-naphthalenyl)-1H-pyrazol-3-yl]oxy]ethyl]morpholine in chloroform in the presence of catalytic amounts of a polymer selected from the group consisting of poly(ethylene glycol), polyvinyl pyrrolidone, poly(acrylic acid), nylon 6/6, polypropylene, poly(tetrafluoroethylene), poly(vinyl acetate), poly(vinyl alcohol), polyacrylamide and polysulfone; and
   b) either evaporating the chloroform or crystallizing in a hot saturated solution of chloroform.

15. A process for the preparation of the phase I form of the hydrochloride salt of 4-[2-[[5-methyl-1-(2-naphthalenyl)-1H-pyrazol-3-yl]oxy]ethyl]morpholine of claim 1 comprising heating the polymorphic phase II form, polymorphic phase III form, polymorphic phase IV form, dioxane solvate or chloroform solvate.

16. A process for the preparation of phase I form of the hydrochloride salt of 4-[2-[[5-methyl-1-(2-naphthalenyl)-1H-pyrazol-3-yl]oxy]ethyl]morpholine comprising the step of heating crystalline forms phase II, phase III and/or phase IV of this compound at a temperature between 140° C. and 170° C.

17. A pharmaceutical composition comprising the solid form defined in claim 1.

18. The solid polymorphic or solvated form of claim 1 which is
   a polymorphic phase I form having a X-ray powder diffraction pattern showing characteristic peaks at a reflection angle [2θ in degrees] of about 5.9, 8.1, 11.3, 11.7, 14.2, 15.1, 15.8, 16.3, 16.8, 17.8, 18.1, 18.6, 19.8, 20.9, 21.9, 22.8, 23.0, 23.2, 23.6, 23.9, 24.3, 25.0, 25.1, 28.0, 28.3, 28.6, 29.0, 29.2, 30.7, and 30.9,
   with the 2θ values being obtained using copper radiation ($Cu_{K\alpha1}$ 1.54060 Å).

19. The solid polymorphic or solvated form of claim 1 which is
   a polymorphic phase II form having a X-ray powder diffraction pattern showing characteristic peaks at a reflection angle [2θ in degrees] of about 5.776, 11.629, 14.558, 15.737, 15.891, 16.420, 16.740, 17.441, 17.635, 18.056, 18.219, 19.232, 19.712, 20.140, 20.685, 21.135, 21.889, 22.108, 22.478, 22.763, 23.219, 23.454, 23.782, 24.689, 25.065, and 25.671,
   with the 2θ values being obtained using copper radiation ($Cu_{K\alpha1}$ 1.54060 Å).

20. The solid polymorphic or solvated form of claim 1 which is
   a polymorphic phase III form having a X-ray powder diffraction pattern showing characteristic peaks at a reflection angle [2θ in degrees] of about 5.437, 5.714, 10.918, 11.546, 12.704, 13.344, 13.984, 14.505, 15.606, 15.824, 16.164, 16.646, 17.333, 17.837, 18.719, 18.878, 19.236, 19.533, 20.142, 20.689, 21.337, 22.008, 22.929, 23.596, 24.748, 25.064, 25.207, 25.737, and 26.148,
   with the 2θ values being obtained using copper radiation ($Cu_{K\alpha1}$ 1.54060 Å).

21. The solid polymorphic or solvated form of claim 1 which is
   a polymorphic phase IV form, preferably having a X-ray powder diffraction pattern showing characteristic peaks at a reflection angle [2θ in degrees] of about 5.805, 11.685, 15.559, 15.804, 16.397, 16.879, 17.357, 17.465, 17.621, 19.112, 19.435, 19.923, 21.224, 21.987, 22.167, 22.412, 2.852, 23.059, 23.359, 23.855, 24.092, 25.722, 26.054, 26.649, and 27.780,
   with the 2θ values being obtained using copper radiation ($Cu_{K\alpha1}$ 1.54060 Å).

22. The solid polymorphic or solvated form of claim 1 which is
   a dioxane solvate having a X-ray powder diffraction pattern showing characteristic peaks at a reflection angle [2θ in degrees] of about 4.734, 9.317, 11.390, 13.614, 14.290, 14.815, 16.211, 16.432, 16.782, 17.741, 18.056, 18.329, 18.724, 19.070, 19.494, 20.436, 20.762, 21.587, 22.000, 22.935, 23.084, 23.551, 23.891, 24.721, and 25.078,
   with the 2θ values being obtained using copper radiation ($Cu_{K\alpha1}$ 1.54060 Å).

23. The solid polymorphic or solvated form of claim 1 which is a) a chloroform solvate having a X-ray powder diffraction pattern showing characteristic peaks at a reflection angle [2θ in degrees] of about 11.370, 13.396, 14.048, 15.010, 15.303, 16.117, 16.804, 17.040, 17.830, 18.029, 18.661, 18.859, 19.190, 20.150, 20.434, 21.424, 22.279, 22.871, 23.449, 23.918, 24.343, 24.709, 24.820, 25.459, and 26.199, with the 2θ values being obtained using copper radiation ($Cu_{K\alpha 1}$ 1.54060 Å).

24. A pharmaceutical composition comprising the solid form defined in claim 18.

25. A pharmaceutical composition comprising the solid form defined in claim 19.

26. A pharmaceutical composition comprising the solid form defined in claim 20.

27. A pharmaceutical composition comprising the solid form defined in claim 21.

28. A pharmaceutical composition comprising the solid form defined in claim 22.

29. A pharmaceutical composition comprising the solid form defined in claim 23.

\* \* \* \* \*